(12) United States Patent
Guertin

(10) Patent No.: US 6,482,951 B2
(45) Date of Patent: Nov. 19, 2002

(54) ISOINDOLIN-1-ONE GLUCOKINASE ACTIVATORS

(75) Inventor: Kevin Richard Guertin, Verona, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/010,978

(22) Filed: Dec. 6, 2001

(65) Prior Publication Data

US 2002/0082260 A1 Jun. 27, 2002

Related U.S. Application Data

(60) Provisional application No. 60/318,715, filed on Sep. 13, 2001, and provisional application No. 60/255,273, filed on Dec. 13, 2000.

(51) Int. Cl.⁷ .................. C07D 401/12; C07D 417/02; C07D 215/38; C07D 277/42
(52) U.S. Cl. .............. 548/159; 544/328; 544/405; 546/163; 546/277.1; 548/195; 548/222; 548/233; 548/305.1; 548/312.1; 548/472; 548/484
(58) Field of Search ................. 544/328, 405; 546/163, 277.1; 548/195, 305.1, 312.1, 159, 222, 233, 472, 484

(56) References Cited

U.S. PATENT DOCUMENTS 5,200,408 A * 4/1993 Bru-Magniez et al.

FOREIGN PATENT DOCUMENTS

| WO | WO 00/58293 | 10/2000 |
| WO | WO 01/83478 | 11/2001 |
| WO | WO 01/85706 | 11/2001 |

OTHER PUBLICATIONS

Printz et al., Ann. Rev. Nutrition, vol. 13 (R. E. Olson, D. M. Bier and D. B. McCormick, eds.) Annual Review, Inc., Palo Alto, CA pp. 463–496 (1993).
Meglasson et al., Amer. J. Physiol., 246, E1–E13 (1984).
Grupe et al., Cell, 83, pp. 69–78 (1995).
Liang et al., Biochem. J., 309, pp. 167–173 (1995).
Glaser et al., New England J. Med., 338, pp. 226–230 (1998).
Ahmar et al., Tetrahedron Lett., pp. 7053–7056 (1989).
O'Donnell et al., J. Org. Chem., 47, pp. 2663–2666 (1982).

* cited by examiner

Primary Examiner—Ceila Chang
Assistant Examiner—Sonya Wright
(74) Attorney, Agent, or Firm—George W. Johnston; Dennis P. Tramaloni; Eileen M. Ebel

(57) ABSTRACT

Isoindolin-1-one-substituted propionamide glucokinase activators which increase insulin secretion in the treatment of type II diabetes.

97 Claims, No Drawings

ISOINDOLIN-1-ONE GLUCOKINASE ACTIVATORS

This application claims the benefit of No. 60/318,715 filed Sep. 13, 2001 and claims the benefit of No. 60/255,273 filed Dec. 13, 2000.

BACKGROUND OF THE INVENTION

Glucokinase (GK) is one of four exokinases that are found in mammals [Colowick, S. P., in *The Enzymes,* Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (~10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J.,* 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226–230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

This invention provides a compound comprising an amide of the formula:

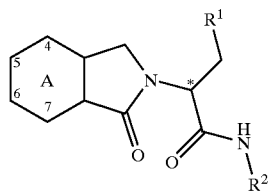

wherein
A is unsubstituted phenyl or phenyl which is mono- or di-substituted with halo or mono-substituted with lower alkyl sulfonyl, lower alkyl thio or nitro; p1 $R^1$ is cycloalkyl having from 3 to 9 carbon atoms or lower alkyl having from 2 to 4 carbon atoms;
$R^2$ is an unsubstituted or mono-substituted five- or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom, which ring may be monocyclic or fused with phenyl at two of its ring carbons, said monosubstituted heteroaromatic ring being monosubstituted at a position on a ring carbon atom other than adjacent to said connecting carbon atom with a substituent selected from the group consisting of halo, lower alkyl, nitro, cyano, perfluoro-lower alkyl; hydroxy, —(CH$_2$)$_n$—OR$^3$, —(CH$_2$)$_n$—C(O)—OR$^3$, —(CH$_2$)$_n$—C(O)—NH—R$^3$, —C(O)C(O)—OR$^3$, or —(CH$_2$)$_n$—NHR$^3$; where $R^3$ is hydrogen or lower alkyl; and n is 0, 1, 2, 3 or 4; or a pharmaceutically acceptable salts or N-oxides thereof.

Preferably $R^2$ is a five- or six-membered heteroaromatic ring connected by a ring carbon atom to the amine group shown in formula I, which five- or six-membered heteroaromatic ring contains from 1 to 3 heteroatoms selected from sulfur, oxygen or nitrogen, with one heteroatom being nitrogen which is adjacent to the connecting ring carbon atom. This ring may be monocyclic or may be fused with phenyl at two of its ring carbons. In accordance with an embodiment of this invention, the adjacent nitrogen in the nitrogen containing heteroaromatic rings may be in the form of an N-oxide where the nitrogen adjacent to the ring carbon atom is converted to an N-oxide. On the other hand, compounds of formula I can be in the form of pharmaceutically acceptable salts.

The compounds of formula I have been found to activate glucokinase in vitro. Glucokinase activators are useful for increasing insulin secretion in the treatment of type II diabetes.

DETAILED DESCRIPTION OF THE INVENTION

This invention provides a compound comprising an amide of the formula I above or a pharmaceutically acceptable salt thereof.

In the compound of formula I, the "." illustrates the asymmetric carbon atom in this compound. The compound of formula I may be present as a racemate at the asymmetric carbon shown. However, the "S" enantiomers, where the amide is in the "S" configuration at the asymmetric carbon, is preferred. When the phenyl ring A is monosubstituted with lower alkyl sulfonyl, nitro or lower alkyl thio, it is preferred that it is substituted at the 5- or 6-position as indicated in formula I. Thus, when A is phenyl substituted with nitro, it is preferred that this substitution be at positions 5 or 6 such as 5-nitro phenyl and 6 nitro phenyl.

In one embodiment of formula I, the $R^2$ ring as described above is a single, or monocyclic (unfused) ring. When $R^2$ is a monocyclic ring, it is preferably substituted or unsubstituted pyridine. In another embodiment of formula I, the $R^2$ ring as described above is a bicyclic ring, i.e. is fused with a phenyl.

As used throughout this application, the term "lower alkyl" includes both straight chain and branched chain alkyl groups having from 1 to 10 and preferably 3 to 9 carbon atoms, such as propyl, isopropyl, heptyl, and especially 2 to 4 carbon atoms.

As used herein, the term "cycloalkyl" signifies a 3- to 9-membered cycloalkyl ring, preferably 5- to 8-membered, for example cyclopentyl, cyclohexyl, cycloheptyl, or cyclooctyl.

As used herein, "perfluoro-lower alkyl" means any lower alkyl group wherein all of the hydrogens of the lower alkyl group are substituted or replaced by fluoro. Among the preferred perfluoro-lower alkyl groups are trifluoromethyl, pentafluoroethyl, heptafluoropropyl, etc.

As used herein, "lower alkyl thio" means a lower alkyl group as defined above bound to the rest of the molecule through the sulfur atom in a thio group.

As used herein, "lower alkyl sulfonyl" means a lower alkyl group as defined above bound to the rest of the molecule through the sulfur atom in a sulfonyl group.

As used herein, the term "halogen" is used interchangeably with the word "halo", and, unless otherwise stated, designates all four halogens, i.e. fluorine, chlorine, bromine, and iodine.

As used herein, the term "N-oxide" means a negatively charged oxygen atom which is covalently linked to a nitrogen which is positively charged in a heteroaromatic ring.

As used herein, "heteroaromatic ring" means a five or six membered unsaturated carbacyclic ring where one or more carbon is replaced by a heteroatom such as oxygen, nitrogen, or sulfur. The heteroaromatic ring may be a single cycle or may be bicyclic, i.e. formed by the fusion of two rings.

The heteroaromatic ring defined by $R^2$ can be an unsubstituted or mono-substituted five- or six-membered heteroaromatic ring having from 1 to 3 heteroatoms selected from the group consisting of oxygen, nitrogen, or sulfur and connected by a ring carbon to the amine of the amide group shown. At least one heteroatom is nitrogen and is adjacent to the connecting ring carbon atom. If present, the other heteroatoms can be sulfur, oxygen or nitrogen. The ring defined by $R^2$ may be a single cycle. Such heteroaromatic rings include, for example, pyridinyl, pyrimidinyl, pyrazinyl, pyridazinyl, isoxazolyl, isothiazolyl, pyrazolyl, thiazolyl, oxazolyl, and imidazolyl. A preferred heteroaromatic ring is pyridinyl. The ring defined by $R^2$ may be a bicyclic, i.e. may be fused with phenyl at two of its free ring carbons. Examples of such rings are benzimidazolyl, benzothiazolyl, quinolynyl, benzooxazolyl, and so forth. The ring defined by $R^2$ is connected via a ring carbon atom to the amide group to form the amides of formula I. The ring carbon atom of the heteroaromatic ring which is connected via the amide linkage to form the compound of formula I cannot contain any substituent. When $R^2$ is an unsubstituted or mono-substituted five-membered heteroaromatic ring, the preferred rings are those which contain a nitrogen heteroatom adjacent to the connecting ring carbon and a second heteroatom adjacent to the connecting ring carbon.

As used herein, $-C(O)OR^3$ represents

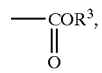

and so forth.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, paratoluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

Also part of this invention are prodrugs of the compound of formula I. By prodrug is meant a metabolic precursor of a drug which when administered to a patient breaks down into the drug and acceptable by-products. Compounds of this invention may be made into any conventional prodrug. One particular prodrug of this invention are the N-oxides as described above. Any individual compound of this invention may be obtained as a prodrug in general.

During the course of the reactions provided below in the Reaction Scheme and discussion, the various functional groups such as the free carboxylic acid or hydroxy groups may be protected via conventional hydrolyzable ester or ether protecting groups. As used herein, the term "hydrolyzable ester or ether protecting groups" designates any ester or ether conventionally used for protecting carboxylic acids or alcohols which can be hydrolyzed to yield the respective carboxyl or hydroxyl group. Exemplary ester groups useful for those purposes are those in which the acyl moieties are derived from a lower alkanoic, aryl lower alkanoic, or lower alkane dicarboxylic acid. Among the activated acids which can be utilized to form such groups are acid anhydrides, acid halides, preferably acid chlorides or acid bromides derived from aryl or lower alkanoic acids. Examples of anhydrides are anhydrides derived from monocarboxylic acid such as acetic anhydride, benzoic acid anhydride, and lower alkane dicarboxylic acid anhydrides, e.g. succinic anhydride as well as chloro formates e.g. trichloro, ethylchloro formate being preferred. A suitable ether protecting group for alcohols are, for example, the tetrahydropyranyl ethers such as 4-methoxy-5,6-dihydroxy-2H-pyranyl ethers. Others are aroylmethylethers such as benzyl, benzhydryl or trityl ethers or α-lower alkoxy lower alkyl ethers, for example, methoxymethyl or allylic ethers or alkyl silylethers such as trimethylsilylether.

Similarly, the term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly acidic conditions from about pH 2 to 3. Particularly preferred amino protecting groups are t-butyl carbamate (BOC), benzyl carbamate (CBZ), and 9-fluorenylmethyl carbamate (FMOC).

In a preferred compound of formula I, $R^1$ is cycloalkyl having from 5 to 8 carbon atoms, and $R^2$ is an unsubstituted or mono-substituted five- or six-membered heteroaromatic ring connected by a ring carbon atom to the amine group shown, which five- or six-membered heteroaromatic ring contains from 1 to 2 heteroatoms selected from sulfur, oxygen or nitrogen, with one heteroatom being nitrogen which is adjacent to the connecting ring carbon atom, which ring may be a single cycle, or may be fused with a phenyl at two of its ring carbons, said mono-substituted heteroaromatic ring being monosubstituted at a position on a ring carbon atom other than adjacent to said connecting carbon atom with a substituent selected from the group consisting of halo or lower alkyl (Formula AB). $R^2$ as described in Formula AB may be a monocyclic ring (Formula A), or may be a bicyclic ring through fusion with phenyl (Formula B). In compounds of formula A, it is particularly preferred that $R^2$ is substituted or unsubstituted pyridine. It is also preferred that $R^1$ is cyclohexyl. Phenyl A is preferably unsubstituted.

In a preferred compound of Formula I, $R^1$ is cyclohexyl and $R^2$ is a monocyclic ring (Formula A-1). It is preferred in compounds of Formula A-1 that phenyl A is unsubstituted. It is particularly preferred that $R^2$ is substituted or unsubstituted pyridine.

In one embodiment of Formula A-1, $R^2$ is unsubstituted pyridine, and in another $R^2$ is a mono-substituted pyridine. Preferably, the substituent is halo such as bromo, fluoro or chloro or lower alkyl such as methyl.

In one embodiment of Formula A-1, $R^2$ is a mono-substituted pyrimidine. Preferably, the substituent is lower alkyl, such as methyl, and phenyl A is unsubstituted. $R^2$ may also be an unsubstituted pyrimidine of Formula A-1. Preferably, phenyl A is unsubstituted or substituted with lower alkyl sulfonyl at the 4 or 7 position.

In one embodiment of Formula A-1, $R^2$ is unsubstituted thiazole. In preferred such compounds, A is phenyl unsubstituted, or substituted with chloro at positions 5 and 6, or substituted with nitro at positions 5 or 6, or substituted with halo or lower alkyl sulfonyl at positions 4 or 7.

In one embodiment of Formula A-1, $R^2$ is a mono-substituted thiazole. Preferably, the substituent is halo, and A is phenyl unsubstituted, or substituted with chloro at positions 5 and 6, or substituted with nitro at positions 5 or 6, or substituted with halo or lower alkyl sulfonyl at positions 4 or 7.

In one embodiment of Formula A-1, $R^2$ is an unsubstituted pyrazine. A is preferably phenyl unsubstituted, or substituted with halo or lower alkyl sulfonyl at positions 4 or 7.

In one embodiment of Formula A-1 where $R^1$ is cylohexyl and $R^2$ is a monocyclic ring, $R^2$ is unsubstituted imidazole, and phenyl and A is preferably unsubstituted phenyl.

In another embodiment of Formula I or of Formula A, phenyl A is unsubstituted, $R^2$ is a monocyclic ring, and it is preferable that $R^2$ is substituted or unsubstituted thiazole. (Formula A-2). In some compounds of Formula A-2, $R^1$ is cyclopentyl, in others, $R^1$ is cycloheptyl, and in others, $R^1$ is cyclooctyl.

In a preferred compound of Formula I where $R^2$ is a bicyclic heteroaromatic ring through fusion with phenyl at two of its ring carbons and $R^1$ is cyclohexyl (Formula B-1).

In compounds of Formula B-1, it is preferred that phenyl A is unsubstituted. It is further preferred that $R^2$ is benzthiazole, benzimidazole, benzoxazole, or quinoline, all preferably unsubstituted.

The compounds of this invention can be prepared by the following Reaction Schemes where phenyl A, $R^1$, $R^2$, and $R^3$ are as in formula I.

Reaction Schemes

Scheme 1

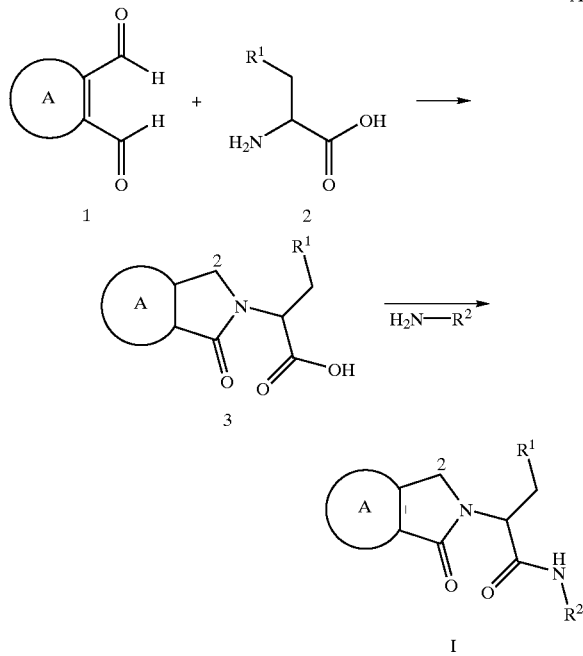

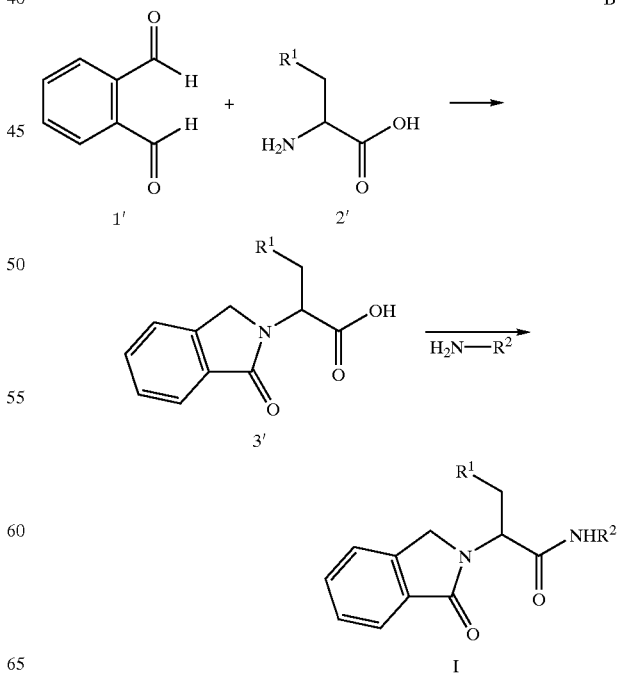

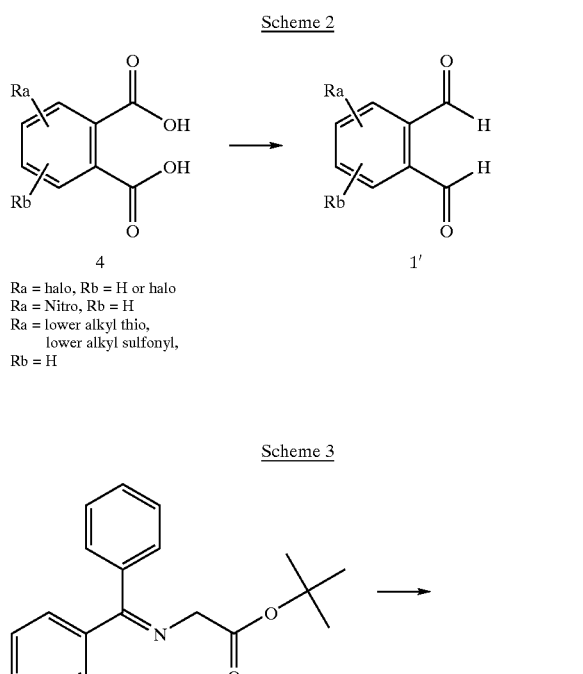

Scheme 2

4
Ra = halo, Rb = H or halo
Ra = Nitro, Rb = H
Ra = lower alkyl thio,
    lower alkyl sulfonyl,
Rb = H

1'

Scheme 3

5

2

The compounds of this invention may be obtained by reacting substituted ortho-phenylene dialdehyde 1 or 1', with amino acid derivative 2 or 2' in a suitable solvent such as acetonitrile, to obtain carboxylic acid derivative 3 or 3'. 3 or 3' may then be coupled with a suitable heteroaromatic amine $H_2N-R^2$ under conventional reaction conditions for amide bond formation to obtain the compounds of formula I.

Compounds of formula I where phenyl A is substituted with halo (obtained from a halo phthalic acid) or nitro are obtained as described in Scheme 2 above where 4 is a suitable commercially available substituted phthalic acid. The substituted ortho-phenylene dialdehydes 1 or 1' may be prepared by reduction of the phthalic acids 4 to the diol intermediates followed by oxidation to provide 1'.

Compounds of formula I where phenyl A is substituted with lower alkyl sulfonyl may be prepared starting from a phthalic acid 4 where Ra is fluoro and Rb is hydrogen by a multistep sequence:
a) conversion to the corresponding dimethyl ester with sulfuric acid in methanol
b) nucleophilic displacement of fluoride with with sodium thiomethoxide in a suitable solvent such as dimethylsulfoxide to provide 4 when Ra is lower alkyl thio,
c) reduction of the resulting phthalic acid 4 when Ra is lower alkyl thio to the diols followed by oxidation to the corresponding ortho-phenylene dialdehyde 1 when Ra is lower alkyl thio
d) reaction of the ortho-phenylene dialdehyde 1 when Ra is lower alkyl thio an amino acid 2 in refluxing acetonitrile to give a mixture of the lower alkyl thio, lower alkyl thio carboxylic acid isomers 3 and e) coupling with $H_2N-R^2$ to provide compounds of formula I where Ra is lower alkyl thio.

Compounds of formula I where Ra is lower alkyl sulfonyl and Rb is hydrogen, can be obtained by first oxidizing the lower alkyl isomers of step (d) above with hydrogen peroxide to form the lower alkyl sulfonyl carboxylic acid of formula 3 (Ra is lower alkyl sulfonyl, Rb is hydrogen and then coupling the resulting carboxylic acid of formula 3 with $H_2N-R^2$ to provide the compound of formula I where Ra is lower alkyl sulfonyl.

Compounds of formula I where $R^1$ is $C_3-C_9$ cycloalkyl or $C_2-C_4$ alkyl (in R, S, or racemic form) are obtained as described above where 2 or 2' is a suitable commercially available amino acid. Amino acid 2 or 2' may also be obtained according to Scheme 3 from 5. 5 is prepared according to the literature procedure (see O'Donnell, M. J.; Polt, R. L. *J. Org. Chem.* 1982, 47, 2663–2666) and may be reacted under basic conditions with a suitable alkyl halide reagent substituted with the desired $R^1$ to obtain, after acidic hydrolysis, any amino acid 2. The alkyl halide reagent may be obtained commercially or made using conventional methods.

Compounds of formula I where $R^2$ is as described in formula I may be obtained by coupling the desired heteroaromatic amine (which is commercially available or can be made by conventional methods) to carboxylic acid derivative 3 or 3' under conventional conditions for reacting an amine with an acid. For compounds of Formula II, the N-oxide heteroaromatic amine (for example 2-aminopyridine-N-oxide) may be coupled to 3 or 3', or the corresponding compound of Formula I may be oxidized at an unsubstituted $R^2$ ring by known methods to obtain an N-oxide.

If it is desired to produce the R or the S isomer of the compound of formula I, this compound can be separated into these isomers by conventional physical or chemical means. One physical means of separation involves resolution of the enantiomeric pairs of compounds of formula I using a high performance liquid chromatography instrument equiped with a chromatographic column loaded with a chiral agent. Among the preferred chemical means is to react the intermediate carboxylic acid 3 or 3' with an optically active base. Any conventional optically active base can be utilized to carry out this resolution. Among the preferred optically active bases are the optically active amine bases such as alpha-methylbenzylamine, quinine, dehydroabietylamine and alpha-methylnaphthylamine. Any of the conventional techniques utilized in resolving organic acids with optically active organic amine bases can be utilized in carrying out this reaction.

In the resolution step, 3 or 3' is reacted with the optically active base in an inert organic solvent medium to produce salts of the optically active amine with both the R and S isomers of 3 or 3'. In the formation of these salts, temperatures and pressure are not critical and the salt formation can take place at room temperature and atmospheric pressure. The R and S salts can be separated by any conventional method such as fractional crystallization. After crystallization, each of the salts can be converted to the respective 3 or 3' in the R and S configuration by hydrolysis with an acid. Among the preferred acids are dilute aqueous acids, i.e., from about 0.001N to 2N aqueous acids, such as aqueous sulfuric or aqueous hydrochloric acid. The configuration of 3 or 3' which is produced by this method of resolution is carried through the entire reaction scheme to produce the desired R or S isomer of formula I or II. The separation of R and S isomers can also be achieved using an enzymatic ester hydrolysis of any lower alkyl ester derivatives of 3 or 3' (see for example, Ahmar, M.; Girard, C.; Block, R, *Tetrahedron Lett,* 1989, 7053), which results in the formation of corresponding chiral acid and chiral ester. The ester and the acid can be separated by any conventional method of separating an acid from an ester. Another preferred method of resolution of racemates of the compounds 3 or 3' is via the formation of corresponding diastereomeric esters or amides. These diastereomeric esters or amides can be prepared by coupling the carboxylic acids 3 or 3' with a chiral alcohol or a chiral amine. This reaction can be carried out using any conventional method of coupling a carboxylic acid with an alcohol or an amine. The corresponding diastereomers of the derivatives of carboxylic acids 3 or 3' can then be separated using any conventional separation methods, such as HPLC. The resulting pure diastereomeric esters or amides can then be hydrolyzed to yield the corresponding pure R or S isomers. The hydrolysis reaction can be carried out using conventional known methods to hydrolyze an ester or an amide without racemization.

This invention will be better understood from the following examples, which are for purposes of illustration and are not intended to limit the invention defined in the claims which follow thereafter.

SYNTHESIS EXAMPLES

Example 1

(S)-3-cyclohexyl-2-(1-oxo-1,3-dihydro-isoindol-2-yl)-
N-thiazol-2-yl-propionamide

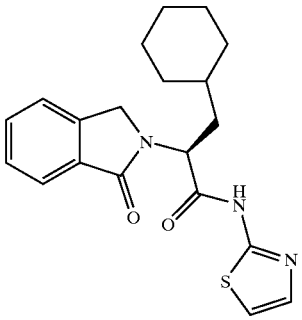

Step A: (S)-3-Cyclohexyl-2-(1-oxo-1,3-dihydro-isoindol-2-yl)-propionic Acid

A mixture of (S)-(+)-α-aminocyclohexanepropionic acid hydrate (5.00 g; 29.2 mmol) and phthalic dicarboxaldehyde (4.21 g; 31.3 mmol) in acetonitrile (120 mL) was refluxed for 20 h under nitrogen. The mixture was allowed to cool to room temperature and further cooled to 0° C. The solid was filtered off and washed once with cold acetonitrile (50 mL) to give 6.54 g (78%) of (S)-3-Cyclohexyl-2-(1-oxo-1,3-dihydro-isoindol-2-yl)-propionic acid as a white solid: EI-HRMS m/e calcd for $C_{17}H_{21}NO_3$ (M$^+$) 287.1521, found 287.1521.

Step B: of (S)-3-cyclohexyl-2-(1-oxo-1,3-dihydro-isoindol-2-yl)-N-thiazol-2-yl-propionamide To a solution of (S)-3-cyclohexyl-2-(1-oxo-1,3-dihydro-isoindol-2-yl)-propionic acid (prepared in Step A, 286 mg; 1.0 mmol), O-benzotriazol-1-yl-N,N,N',N',-tetramethyluronium hexafluorophosphate (BOP, 500 mg; 1.1 mmol) and 2-aminoihiazole (125 mg; 1.2 mmol) in dry methylene chloride (10 mL) at 0° C. was added N,N-diisopropylethylamine (0.55 mL; 3.1 mmol) dropwise. The mixture was allowed to warm to room temperature and stirred overnight. The mixture was then partitioned with water and the organic layer washed with brine, dried (MgSO$_4$), filtered and concentrated in vacuo to give a crude residue. Flash chromatography (Biotage 40S; eluent: 3% methanol/methylene chloride) provided 325 mg (75%) of (S)-3-cyclohexyl-2-(1-oxo-1,3-dihydro-isoindol-2-yl)-N-thiazol-2-yl-propionamide as a light brown foam: EI-HRMS m/e calcd for $C_{20}H_{23}N_3O_2S$ (M$^+$) 369.1511, found 369.1513.

Example 2

(S)-N-(5-Chloro-thiazol-2-yl)-3-cyclohexyl-2-
(1-oxo-1,3-dihydro-isoindol-2-yl) propionamide

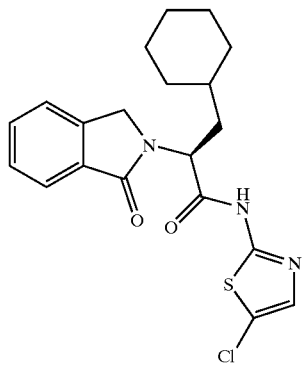

This compound was prepared via BOP coupling of (S)-3-cyclohexyl-2-(1-oxo-1,3-dihydro-isoindol-2-yl)-propionic acid (prepared in Step A of Example 1; 120 mg; 0.42 mmol) and 2-amino-5-chlorothiazole hydrochloride (90 mg; 0.51 mmol) in a manner similar to that used for the preparation of (S)-3-cyclohexyl-2-(1-oxo-1,3-dihydro-isoindol-2-yl)-N-thiazol-2-yl-propionamide as outlined in Example 1, Step B) to provide N-(5-Chloro-thiazol-2-yl)-3-cyclohexyl-2-(1-oxo-1,3-dihydro-isoindol-2-yl) propionamide as a white solid in 59% yield: EI-HRMS m/e calcd for $C_{20}H_{22}ClN_3O_2S$ (M$^+$) 403.1121, found 403.1124.

Example 3

(S)-N-(5-Bromo-thiazol-2-yl)-3-cyclohexyl-2-
(1-oxo-1,3-dihydro-isoindol-2-yl)-propionamide

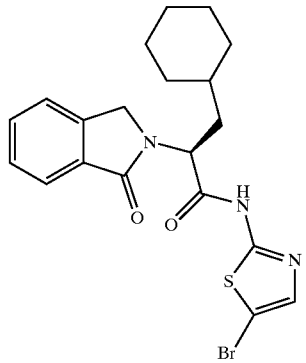

To a suspension of (S)-3-cyclohexyl-2-(1-oxo-1,3-dihydro-isoindol-2-yl)-N-thiazol-2-yl-propionamide (Prepared in Example 1; 21 mg; 0.06 mmol) and N-bromosuccinimide (11 mg; 0.06 mmol) in anhydrous carbon tetrachloride (1.0 mL) was added benzoyl peroxide (1 mg; 0.004 mmol). The mixture was stirred at 95° C. in a sealed tube. After 1.5 h, N-bromosuccinimide (2 mg) and benzoyl peroxide (1 mg) were added and the mixture stirred for 30 min. further. The mixture was allowed to cool to room temperature and the solvent removed in vacuo. The residue was taken up into ethyl acetate and washed with water. The organic extract was washed with brine, dried over sodium sulfate, filtered and concentrated in vacuo. The crude residue was purified by flash chromatography (Biotage 12S, eluent: 20% ethyl acetate/hexanes to give 15 mg (58%) of N-(5-Bromo-thiazol-2-yl)-3-cyclohexyl-2-(1-oxo-1,3-dihydro-isoindol-2-yl)-propionamide as a grey foam: EI-HRMS m/e calcd for $C_{20}H_{23}BrN_3O_2S$ ($M^+$) 447.0616, found 447.0623.

Example 4

(S)-3-Cyclohexyl-2-(5,6-dichloro-1-oxo-1,3-dihydro-isoindol-2-yl)-N-thiazol-2-yl-propionamide

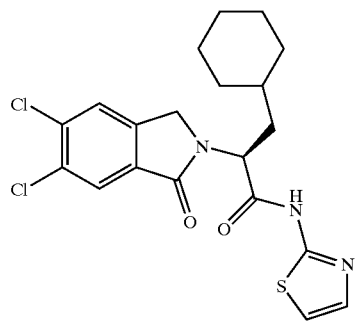

Step A: 4,5-dichloro-1,2-di-hydroxymethyl Benzene

To a stirred solution of borane tetrahydrofuran complex (45 mL of 1.5 M solution in tetrahydrofuran/diethyl ether) cooled to 0° C. under nitrogen was added a solution of 4,5-dichlorophthalic acid (5.013 g; 21.1 mmol) in tetrahydrofuran (35 mL) dropwise over a 20 minute period. At the end of the addition, the mixture was allowed to stir for 2.5 h at 0° C. The mixture was quenched by slow addition of methanol until gas evolution ceased. The mixture was allowed to stir at room temperature for 30 minutes and the solvent removed in vacuo. The residue was taken up into ethyl acetate, washed with saturated sodium bicarbonate solution followed by brine solution. The organic extract was dried (sodium sulfate), filtered and concentrated in vacuo to give 4.41 g (100%) of 4,5-dichloro-1,2-di-hydroxymethyl benzene as a white solid: ES-LRMS calcd for $C_8H_7Cl_2O_2$ ($M^+$-1) 205, found 205.

Step B: 4,5-dichlorophthalic-1,2-dicarboxaldehyde

To a stirred solution of oxalyl chloride (2.6 mL; 29.2 mmol) in anhydrous methylene chloride (35 mL) under nitrogen at −78° C. was added a solution of dimethyl sulfoxide (4.2 mL; 59.1 mmol) in methylene chloride (10 mL) dropwise. The solution was stirred for 10 minutes and then a solution of 4,5-dichloro-1,2-di-hydroxymethyl benzene (2.50 g; 12.1 mmol) dissolved in 16 mL of 1:1 methylene chloride/dimethyl sulfoxide was added dropwise. The resulting mixture was stirred at −78° C. for 2 h. Triethylamine (30 mL; 17.6 mmol) was added slowly over 15 minutes and the mixture allowed to warm to roome temperature for 2 h. The mixture was diluted with cold water (150 mL) and extracted with methylene chloride. The extracts were washed with 1N HCl, dried over sodium sulfate and concentrated to give 2.58 g of 4,5-dichlorophthalic-1,2-dicarboxaldehyde as a yellow solid: ES-LRMS calcd for $C_8H_3O_2$ ($M^+$-1) 201, found 201.

Step C: (S)-3-cyclohexyl-2-(5,6-dichloro-1-oxo-1,3-dihydro-isoindol-2-yl)-propionic Acid A mixture of (S)-(+)-α-aminocyclohexanepropionic acid hydrate (1.05 g; 5.83 mmol) and 4,5-dichlorophthalic dicarboxaldehyde (prepared in Step B; 1.25 g; 5.86 mmol) in acetonitrile (35 mL) was refluxed under argon for 72 h. The mixture was then allowed to cool and allowed to stand at room temperature for 2 h. The solid was filtered off and washed once with cold acetonitrile to give 1.33 g (64%) of (S)-3-cyclohexyl-2-(5,6-dichloro-1-oxo-1,3-dihydro-isoindol-2-yl)-propionic acid as a light brown solid: EI-HRMS m/e calcd for $C_{17}H_{19}Cl_2NO_3$ ($M^+$) 355.0742, found 355.0747.

Step D: (S)-3-Cyclohexyl-2-(5,6-dichloro-1-oxo-1, 3-dihydro-isoindol-2-yl)-N-thiazol-2-yl-propionamide BOP coupling of (S)-3-cyclohexyl-2-(5,6-dichloro-1-oxo-1,3-dihydro-isoindol-2-yl)-propionic acid (prepared in Step C; 248 mg; 0.70 mmol) and 2-aminothiazole (91 mg; 0.88 mmol) in a manner similar to that used for the preparation of (S)-3-cyclohexyl-2-(1-oxo-1,3-dihydro-isoindol-2-yl)-N-thiazol-2-yl-propionamide (outlined in Example 1, Step B) to provide (S)-3-Cyclohexyl-2-(5,6-dichloro-1-oxo-1,3-dihydro-isoindol-2-yl)-N-thiazol-2-yl-propionamide as a beige foam in 35% yield: EI-HRMS m/e calcd for $C_{20}H_{21}Cl_2N_3O_2S$ ($M^+$) 437.0731, found 437.0725.

Example 5

(S)-N-(5-Chloro-thiazol-2-yl)-3-cyclohexyl-2-(5,6-dichloro-1-oxo-1,3-dihydro-isoindol-2-yl)propionamide

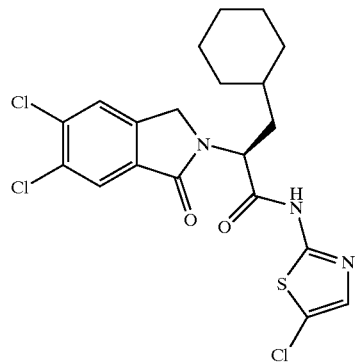

This compound was prepared via BOP coupling of (S)-3-cyclohexyl-2-(5,6-dichloro-1-oxo-1,3-dihydro-isoindol-2-yl)-propionic acid (prepared in Example 4, Step C; 250 mg; 0.70 mmol) and 2-amino-5-chlorothiazole hydrochloride (154 mg; 0.88 mmol) in a manner similar to that used for the preparation of (S)-3-cyclohexyl-2-(1-oxo-1,3-dihydro-isoindol-2-yl)-N-thiazol-2-yl-propionamide (outlined in Example 1, Step B) to provide N-(5-Chloro-thiazol-2-yl)-3-cyclohexyl-2-(5,6-dichloro-1-oxo-1,3-dihydro-isoindol-2-yl)-propionamide as a beige solid in 37% yield: EI-HRMS m/e calcd for $C_{20}H_{20}Cl_3N_3O_2S$ ($M^+$) 471.0342, found 471.0345.

Example 6

(S)-N-(5-Bromo-thiazol-2-yl)-3-cyclohexyl--2-(5,6-dichloro-1-oxo-1,3-dihydro-isoindol-2-yl)-propionamide

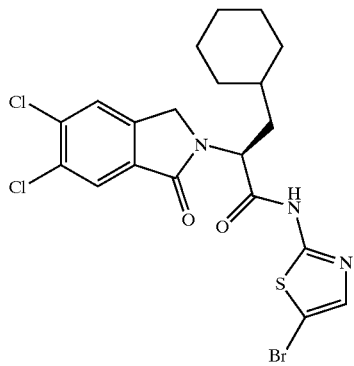

This compound was prepared via BOP coupling of (S)-3-cyclohexyl-2-(5,6-dichloro-1-oxo-1,3-dihydro-isoindol-2-yl)-propionic acid (prepared in Example 4, Step C; 248 mg; 0.70 mmol) and 2-amino-5-bromothiazole hydrochloride (154 mg; 0.89 mmol) in a manner similar to that used for the preparation of (S)-3-cyclohexyl-2-(1-oxo-1,3-dihydro-isoindol-2-yl)-N-thiazol-2-yl-propionamide (outlined in Example 1, Step B) to provide N-(5-Bromo-thiazol-2-yl)-3-cyclohexyl-2-(5,6-dichloro-1-oxo-1,3-dihydro-isoindol-2-yl)-propionamide as a beige solid in 40% yield: EI-HRMS m/e calcd for $C_{20}H_{20}BrCl_2N_3O_2S$ ($M^+$) 514.9837, found 514.9836.

Example 7

(S)-N-(1H-Benzoimidazol-2-yl)-3-cyclohexyl-2-(1-oxo-1,3-dihydro-isoindol-2-yl)-propionamide

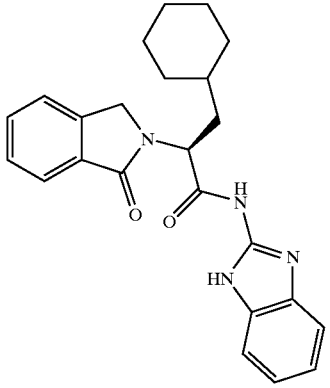

This compound was prepared via BOP coupling of (S)-3-cyclohexyl-2-(1-oxo-1,3-dihydro-isoindol-2-yl)-propionic acid (prepared in Example 1, Step A, 287 mg; 1.0 mmol and 2-amino-benzimidazole (119 mg; 1.0 mmol) in a manner similar to that used for the preparation of (S)-3-cyclohexyl-2-(1-oxo-1,3-dihydro-isoindol-2-yl)-N-thiazol-2-yl-propionamide (outlined in Example 9, Step B) to provide crude N-(5-Bromo-thiazol-2-yl)-3-cyclohexyl-2-(5,6-dichloro-1-oxo-1,3-dihydro-isoindol-2-yl)-propionamide. The crude product was purified by reverse-phase HPLC (Rainin Dynamax SD-1 instrument) using a gradient of 10% acetonitrile/water/0.1% trifluoroacetic acid to 100% acetonitrile on a $C_{18}$ column. The combined fractions containing product were concentrated to remove most of the acetonitrile and then extracted with ethyl acetate. The extracts were dried (sodium sulfate) and concentrated in vacuo to give 240 mg (60%) of N-(1H-Benzoimidazol-2-yl)-3-cyclohexyl-2-(1-oxo-1,3-dihydro-isoindol-2-yl)-propionamide as a white solid: EI-HRMS m/e calcd for $C_{24}H_{26}N_4O_2$ ($M^+$) 402.2056, found 402.2056.

Example 8

(S)-N-Benzothiazol-2-yl-3-cyclohexyl-2-(1-oxo-1,3-dihydro-isoindol-2-yl)-propionamide

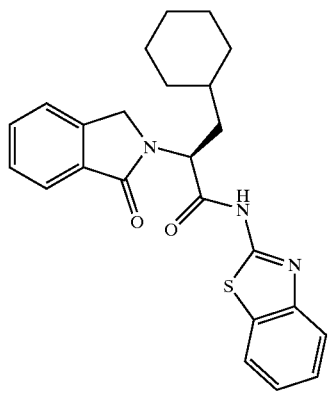

This compound was prepared via BOP coupling of (S)-3-cyclohexyl-2-(1-oxo-1,3-dihydro-isoindol-2-yl)-propionic acid (prepared in Example 1, Step A, 144 mg; 0.5 mmol) and 2-amino-benzothiazole (81 mg; 0.55 mmol) in a manner similar to that used for the preparation of (S)-3-cyclohexyl-2-( 1-oxo-1,3-dihydro-isoindol-2-yl)-N-thiazol-2-yl-propionamide (outlined in Example 9, Step B) to provide crude N-Benzothiazol-2-yl-3-cyclohexyl-2-( 1-oxo-1,3-dihydro-isoindol-2-yl)-propionamide. The crude product was purified by flash chromatography (Merck Silica gel 60, 230–400 mesh, eluent: 35% ethyl acetate/hexanes) to give 185 mg (44%) of N-Benzothiazol-2-yl-3-cyclohexyl-2-( 1-oxo-1,3-dihydro-isoindol-2-yl)-propionamide as a white solid: EI-HRMS m/e calcd for $C_{24}H_{25}N_3O_2S$ ($M^+$) 419.1667, found 419.1661.

Example 9

(R)-3-cyclohexyl-2-(1-oxo-1,3-dihydro-isoindol-2-yl)--N-thiazol-2-yl-propionamide

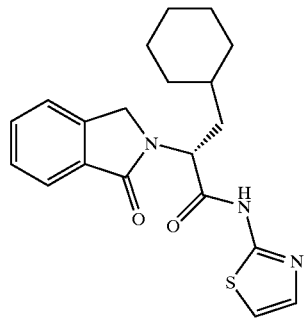

Step A: (R)-3-Cyclohexyl-2-(1-oxo-1,3-dihydro-isoindol-2-yl)-propionic Acid

A mixture of (R)-(+)-α-aminocyclohexanepropionic acid hydrochloride (2.69 g; 15.7 mmol) and phthalic dicarboxaldehyde (2.50 g; 14.6 mmol) in acetonitrile (60 mL) was refluxed for 42 h under nitrogen. The mixture was allowed to cool to room temperature and further cooled to 0° C. The solid was filtered off and washed once with cold acetonitrile to give 2.65 g (63%) of (R)-3-Cyclohexyl-2-(1-oxo-1,3-dihydro-isoindol-2-yl)-propionic acid as a white solid: EI-HRMS m/e calcd for $C_{17}H_{21}NO_3$ ($M^+$) 287.1521, found 287.1523.

Step B: (R)-3-cyclohexyl-2-(1-oxo-1,3-dihydro-isoindol-2-yl)-N-thiazol-2-yl-propionamide To a solution of (R)-3-cyclohexyl-2-(1-oxo-1,3-dihydro-isoindol-2-yl)-propionic acid (prepared in Step A, 144 mg; 0.5 mmol), O-benzotriazol-1-yl-N,N,N',N',-tetramethyluronium hexafluorophosphate (BOP, 268 mg; 0.55 mmol) and 2-aminothiazole (50 mg; 0.5 mmol) in dry methylene chloride (3 mL) at room temperature was added N,N-diisopropylethylamine (0.20 mL; 1.15 mmol) dropwise. The mixture was allowed to stir for 1 h. The mixture was then diluted with methylene chloride and washed with water. The organic layer was dried ($Na_2SO_4$), filtered and concentrated in vacuo to give a crude residue. Flash chromatography (Merck Silica gel 60, 230–400 mesh, eluent: 30% ethyl acetate/hexanes) provided 150 mg (81%) of (R)-3-cyclohexyl-2-(1-oxo-1,3-dihydro-isoindol-2-yl)-N-thiazol-2-yl-propionamide as an off white foam: EI-HRMS m/e calcd for $C_{20}H_{23}N_3O_2S$ ($M^+$) 369.1511, found 369.1511.

Example 10

(S)-3-Cyclohexyl-2-(1-oxo-1,3-dihydro-isoindol-2-yl)-N-quinolin-2-yl-propionamide

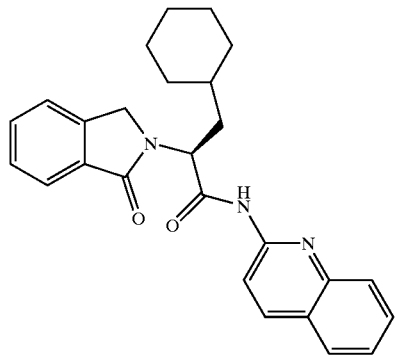

This compound was prepared via BOP coupling of (S)-3-cyclohexyl-2-(1-oxo-1,3-dihydro-isoindol-2-yl)-propionic acid (prepared in Step A of Example 1; 288 mg; 1.0 mmol) and 2-aminoquinoline (180 mg; 1.2 mmol) in a manner similar to that used for the preparation of (S)-3-cyclohexyl-2-(1-oxo-1,3-dihydro-isoindol-2-yl)-N-thiazol-2-yl-propionamide as outlined in Example 1, Step B) to provide 3-Cyclohexyl-2-(1-oxo-1,3-dihydro-isoindol-2-yl)-N-quinolin-2-yl-propionamide as a white solid in 99% yield: EI-HRMS m/e calcd for $C_{26}H_{27}N_3O_2$ ($M^+$) 413.2103, found 413.2103.

Example 11

11.1. (S)-3-Cyclohexyl-2-(5-nitro-1-oxo-1,3-dihydro-isoindol-2-yl)-N-thiazol-2-yl-propionamide and 11.2. (S)-3-Cyclohexyl-2-(6-nitro-1-oxo-1,3-dihydro-isoindol-2-yl)-N-thiazol-2-yl-propionamide

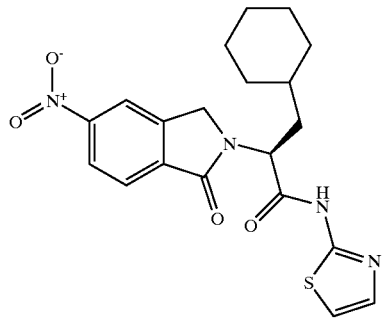

Step A: 4-nitro-1,2-di-hydroxymethyl Benzene

To a stirred solution of borane.tetrahydrofuran complex (70 mL of 1.5 M solution in tetrahydrofuran/diethyl ether) cooled to 0° C. under nitrogen was added a solution of 4-nitrophthalic acid (7.01 g; 33.2 mmol) in tetrahydrofuran (50 mL) dropwise over a 20 minute period. At the end of the addition, the mixture was allowed to stir for 3.5 h at 0° C. The mixture was allowed to warm to room temperature and then refluxed for 18 h. The mixture was allowed to cool to room temperature, quenched with methanol and concentrated in vacuo. The residue was taken up into ethyl acetate, washed with saturated sodium bicarbonate solution followed by brine solution. The organic extract was dried (sodium sulfate), filtered and concentrated in vacuo to give 5.61 g (92%) of 4-nitro-1,2-di-hydroxymethyl benzene as a white solid: ES-LRMS calcd for $C_8H_8NO_4$ ($M^+$-1) 182, found 182.

Step B: 4-nitro-ortho-phenylene-1,2-dicarboxaldehyde

To a stirred solution of oxalyl chloride (4.90 mL; 55.0 mmol) in anhydrous methylene chloride (60 mL) under nitrogen at −78° C. was added a solution of dimethyl sulfoxide (8.20 mL; 115 mmol) in methylene chloride (20 mL) dropwise. The solution was stirred for 10 minutes and then a solution of 4-nitro-1,2-di-(hydroxymethyl) benzene (3.99 g; 21.8 mmol) dissolved in 20 mL of 1:1 methylene chloride/dimethyl sulfoxide was added dropwise. The resulting mixture was stirred at −78° C. for 3 h. Triethylamine (60 mL; 426 mmol) was added slowly over 15 minutes and the mixture allowed to warm to room temperature for 2 h. The mixture was diluted with cold water (300 mL) and extracted with methylene chloride. The extracts were washed with 1N HCl, dried over sodium sulfate and concentrated to give crude 4-nitro-ortho-phenylene-1,2-dicarboxaldehyde which was further purified by flash chromatography (Biotage 40M, eluent: 35% ethyl acetate/hexanes) to give 2.5 g (64%) of 4-nitro-1,2-dicarboxaldehyde which was estimated to be approximately 40% pure by NMR. ES-LRMS calcd for $C_8H_4NO_4$ ($M^+$-1) 178, found 178.

Step C: (S)-3-cyclohexyl-2-(5-nitro-1-oxo-1,3-dihydro-isoindol-2-yl)-propionic Acid A mixture of (S)-(+)-α-aminocyclohexanepropionic acid hydrate (0.708 g; 3.93 mmol) and 4-nitrophthalic dicarboxaldehyde (prepared in Step B; 2.02 g; 3.95 mmol) in acetonitrile (20 mL) was heated to reflux under argon. An additional quantity of (S)-(+)-α-aminocyclohexanepropionic acid hydrate (0.775 g; 4.30 mmol) was added portionwise over a 2 hour period and the mixture allowed to reflux overnight. The mixture was allowed to cool to room temperature and the solid filtered off and washed once with cold acetonitrile to give a beige solid (0.511 g) consisting of (S)-3-cyclohexyl-2-(5-nitro-1-oxo-1, 3-dihydro-isoindol-2-yl)-propionic acid together with regioisomeric (S)-3-cyclohexyl-2-(6-nitro-1-oxo-1,3-dihydro-isoindol-2-yl)-propionic acid in a ratio of 1:2.7. The filtrate was then concentrated in vacuo and the residue recrystallized from acetonitrile to give a second crop of product (1.01 g) which appeared to be further enriched with (S)-3-cyclohexyl-2-(5-nitro-1-oxo-1,3-dihydro-isoindol-2-yl)-propionic acid. The mixture had ES-LRMS calcd for $C_{17}H_{19}N_2O_5$ ($M^+-1$) 331, found 331.

Step D: (S)-3-Cyclohexyl-2-(5-nitro-1-oxo-1,3-dihydro-isoindol-2-yl)-N-thiazol-2-yl-propionamide and (S)-3-Cyclohexyl-2-(6-nitro-1-oxo-1,3-dihydro-isoindol-2-yl)-N-thiazol-2-yl-propionamide.

BOP coupling of (S)-3-cyclohexyl-2-(5-nitro-1-oxo-1,3-dihydro-isoindol-2-yl)-propionic acid (ca. 1:1 mixture of regioisomers, prepared in Step C; 301 mg; 0.91 mmol) and 2-aminothiazole (116 mg; 1.12 mol) in a manner similar to that used for the preparation of (S)-3-cyclohexyl-2-(1-oxo-1,3-dihydro-isoindol-2-yl)-N-thiazol-2-yl-propionamide (as outlined in Example 1, Step B) provided after chromatography (Biotage 40M, eluent: 30% ethyl acetate/hexanes) 131 mg of 3-Cyclohexyl-2-(5-nitro-1-oxo-1,3-dihydro-isoindol-2-yl)-N-thiazol-2-yl-propionamide: EI-HRMS m/e calcd for $C_{20}H_{22}N_4O_4S$ ($M^+$) 414.1362, found 414.1362 and 121 mg of regioisomeric 3-Cyclohexyl-2-(6-nitro-1-oxo-1,3-dihydro-isoindol-2-yl)-N-thiazol-2-yl-propionamide: EI-HRMS m/e calcd for $C_{20}H_{22}N_4O_4S$ ($M^+$) 414.1362, found 414.1368.

Example 12

(S)-N-(5-Chloro-thiazol-2-yl)-3-cyclohexyl-2-(5-nitro-1-oxo-1,3-dihydro-isoindol-2-yl)-propionamide and 12.2. (S)-N-(5-Chloro-thiazol-2-yl)- 3-cyclohexyl-2-(6-nitro-1-oxo-1,3-dihydro-isoindol-2-yl)-propionamide

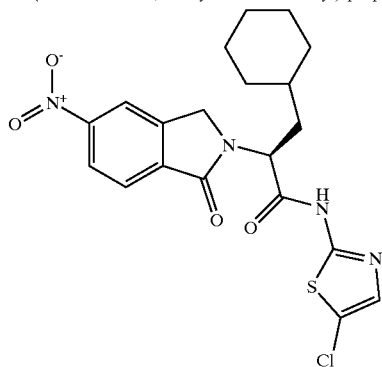

BOP coupling of ((S)-3-cyclohexyl-2-(5-nitro-1-oxo-1,3-dihydro-isoindol-2-yl)-propionic acid (ca. 1:1 mixture of 5,6-regioisomers, prepared in Step C; 307 mg; 0.92 mmol) and 2-amino-5-chlorothiazole hydrochloride (360 mg; 2.04 mmol) in a manner similar to that used for the preparation of (S)-3-cyclohexyl-2-(1-oxo-1,3-dihydro-isoindol-2-yl)-N-thiazol-2-yl-propionamide (as outlined in Example 1, Step B) provided after chromatography, (Biotage 40M, eluent: 25% ethyl acetate/hexanes) 134 mg of (S)- N-(5-Chloro-thiazol-2-yl)-3-cyclohexyl-2-(5-nitro-1-oxo-1,3-dihydro-isoindol-2-yl)-propionamide: EI-HRMS m/e calcd for $C_{20}H_{21}ClN_4O_4S$ ($M^+$) 448.0972, found 448.0970 and 111 mg of regioisomeric (S)-N-(5-Chloro-thiazol-2-yl)-3-cyclohexyl-2-(6-nitro-1-oxo-1,3-dihydro-isoindol-2-yl)-propionamide: EI-HRMS m/e calcd for $C_{20}H_{21}ClN_4O_4S$ ($M^+$) 448.0972, found 448.0972.

Example 13

13.1 (S)-N-(5-Chloro-thiazol-2-yl)-3-cyclohexyl-2-(4-fluoro-1-oxo-1,3-dihydro-isoindol-2yl)-propionamide and 13.2. (S)-N-(5-Chloro-thiazol -2-yl)-3-cyclohexyl-2-(7-fluoro-1-oxo-1,3-dihydro-isoindol-2-yl)-propionamide

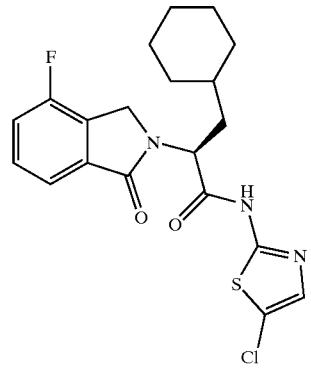

Step A: 3-fluoro-1,2-di-(hydroxymethyl) benzene

To a stirred solution of borane.tetrahydrofuran complex (50 mL of 1.5 M solution in tetrahydrofuran/diethyl ether) cooled to 0° C. under argon was added a solution of 3-fluorophthalic acid (4.51 g; 24.0 mmol) in tetrahydrofuran (40 mL) dropwise over a 15 minute period. At the end of the addition, the mixture was allowed to stir for 2 h at 0° C. The mixture was allowed to warm to room temperature and then refluxed for 20 h. The mixture was allowed to cool to room temperature, quenched with methanol (30 mL) and concentrated in vacuo. The residue was taken up into ethyl acetate (150 mL), washed with saturated sodium bicarbonate solution. The aqueous layer was further extracted with ethyl acetate (2×125 mL) and the combined extracts were washed with brine solution. The organic extract was dried (sodium sulfate), filtered and concentrated in vacuo to give 3.73 g (99%) of 3-fluoro-1,2-di-(hydroxymethyl) benzene as a white solid: ES-LRMS calcd for $C_8H_8FO_2$ ($M^+-1$) 155, found 155.

Step B: 3-fluorophthalic Dicarboxaldehyde

To a stirred solution of oxalyl chloride (2.80 mL; 31.5 mmol) in anhydrous methylene chloride (35 mL) under nitrogen at −78° C. was added a solution of dimethyl sulfoxide (4.6 mL; 64.7 mmol) in methylene chloride (10 mL) dropwise. The solution was stirred for 30 minutes and then a solution of 3-fluoro-1,2-di-hydroxymethyl benzene (2.00 g; 12.8 mmol) dissolved in 20 mL of 1:1 methylene chloride/dimethyl sulfoxide was added dropwise. The resulting mixture was stirred at −78° C. for 2.5 h. Triethylamine (35 mL; 248.6 mmol) was added slowly over 15 minutes and the mixture stirred for 30 minutes at −78° C. then allowed to warm to room temperature over 4 h. The mixture was poured into cold water (200 mL) and extracted with methylene chloride. The extracts were washed with 1N HCl, brine and then dried (sodium sulfate) and concentrated to give crude 3-fluorophthalic dicarboxaldehyde which was not further purified: ES-LRMS calcd for $C_8H_4FO_2$ ($M^+-1$) 151, found 151.

Step C: (S)-3-cyclohexyl-2-(4-fluoro-1-oxo-1,3-dihydro-isoindol-2-yl)-propionic acid A mixture of (S)-(+)-α-aminocyclohexanepropionic acid hydrate (0.565 g; 3.14 mmol) and 3-fluorophthalic dicarboxaldehyde (prepared in Step B; 1.60 g; 3.16 mmol) in acetonitrile (20 mL) was heated to reflux under argon. An additional quantity of (S)-(+)-α-aminocyclohexanepropionic acid hydrate (0.437 g; 2.43 mmol) was added portionwise over a 7 hour period and the mixture allowed to reflux for 72 h. The mixture was allowed to cool to room temperature for 3 h and then stored in the fridge for 1 h. The solid was filtered off and washed once with cold acetonitrile to give a white solid (1.39 g, 77%) consisting of (S)-3-cyclohexyl-2-(4-fluoro-1-oxo-1,3-dihydro-isoindol-2-yl)-propionic acid together with regio-isomeric (S)-3-cyclohexyl-2-(7-fluoro-1-oxo-1,3-dihydro-isoindol-2-yl)-propionic acid in a ratio of about 1:1: ES-LRMS calcd for $C_{17}H_{19}FNO_3$ ($M^+$ –1) 304, found 304.

Step D: (S)-N-(5-Chloro-thiazol-2-yl)-3-cyclohexyl-2-(4-fluoro-1-oxo-1,3-dihydro-isoindol-2-yl)-propionamide and (S)-N-(5-Chloro-thiazol-2-yl)-3-cyclohexyl-2-(7-fluoro-1-oxo-1,3-dihydro-isoindol-2-yl)-propionamide.

BOP coupling of (S)-3-cyclohexyl-2-(4-fluoro-1-oxo-1,3-dihydro-isoindol-2-yl)-propionic acid (ca. 1:1 mixture of regioisomers, prepared in Step C; 501 mg; 1.64 mmol) and 2-amino-5-chlorothiazole hydrochloride (643 mg; 3.64 mmol) in a manner similar to that used for the preparation of (S)-3-cyclohexyl-2-(1-oxo-1,3-dihydro-isoindol-2-yl)-N-thiazol-2-yl-propionamide as outlined in Example 9, Step B) provided after normal phase HPLC (Waters Prep. 500, loaded on column with methylene chloride, eluent: 20% ethyl acetate/hexanes) 194 mg of (S)-N-(5-Chloro-thiazol-2-yl)-3-cyclohexyl-2-(4-fluoro-1-oxo-1,3-dihydro-isoindol-2-yl)-propionamide: EI-HRMS m/e calcd for $C_{20}H_{21}ClFN_3O_2S$ ($M^+$) 421.1027, found 421.1024; and 173 mg of regioisomeric (S)-N-(5-Chloro-thiazol-2-yl)-3-cyclohexyl-2-(7-fluoro-1-oxo-1,3-dihydro-isoindol-2-yl)-propionamide: EI-HRMS m/e calcd for $C_{20}H_{21}ClFN_3O_2S$ ($M^+$) 421.1027, found 421.1031.

Example 14

3-Cyclohexyl-2-(1-oxo-1,3-dihydro-isoindol-2-yl)-N-pyrimidin-4-yl-propionamide

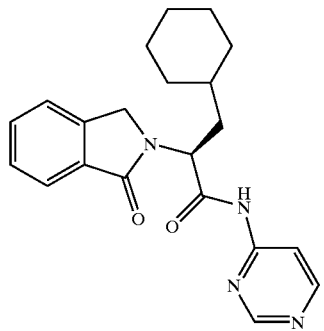

BOP coupling of (S)-3-Cyclohexyl-2-(1-oxo-1,3-dihydro-isoindol-2-yl)-propionic acid (prepared in Example 1, Step A; 287 mg; 1.00 mmol) and 4-aminopyrimidine (108 mg; 1.14 mmol) in a manner similar to that used for the preparation of (R)-3-cyclohexyl-2-(1-oxo-1,3-dihydro-isoindol-2-yl)-N-thiazol-2-yl-propionamide (outlined in Example 9, Step B) provided after flash chromatography (Merck Silica gel 60, 230–400 mesh, eluent: 50% ethyl acetate/hexanes) 271 mg (74%)of 3-Cyclohexyl-2-(1-oxo-1,3-dihydro-isoindol-2-yl)-N-pyrimidin-4-yl-propionamide as a white foam: EI-HRMS m/e calcd for $C_{21}H_{24}N_4O_2$ ($M^+$) 364.1899, found 364.1893.

Example 15

(S)-3-Cyclohexyl-2-(1-oxo-1,3-dihydro-isoindol-2-yl)-N-pyrazin-2-yl-propionamide

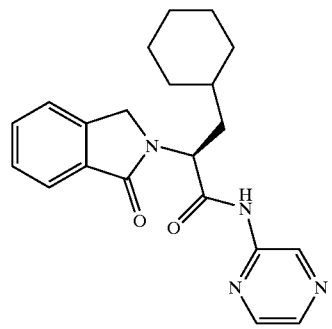

BOP coupling of (S)-3-Cyclohexyl-2-(1-oxo-1,3-dihydro-isoindol-2-yl)-propionic acid (prepared in Example 1, Step A; 287 mg; 1.00 mmol) and 2-aminopyrazine (95 mg; 1.00 mmol) in a manner similar to that used for the preparation of (R)-3-cyclohexyl-2-(1-oxo-1,3-dihydro-isoindol-2-yl)-N-thiazol-2-yl-propionamide (outlined in Example 9, Step B) provided after flash chromatography (Merck Silica gel 60, 230–400 mesh, eluent: 50% ethyl acetate/hexanes) 350 mg (96%)of (S)-3-Cyclohexyl-2-(1-oxo-1,3-dihydro-isoindol-2-yl)-N-pyrazin-2-yl-propionamide as a white foam: EI-HRMS m/e calcd for $C_{21}H_{24}N_4O_2$ ($M^+$) 364.1899, found 364.1908.

Example 16

(S)-N-Benzooxazol-2-yl-3-cyclohexyl-2-(1-oxo-1,3-dihydro-isoindol-2-yl)-propionamide

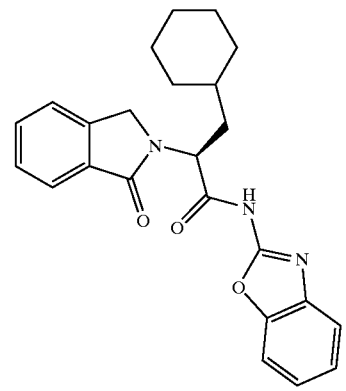

BOP coupling of (S)-3-Cyclohexyl-2-(1-oxo-1,3-dihydro-isoindol-2-yl)-propionic acid (prepared in Example 1, Step A; 144 mg; 0.50 mmol) and 2-aminobenzoxazole (67 mg; 0.50 mmol) in a manner similar to that used for the preparation of (R)-3-cyclohexyl-2-(1-oxo-1,3-dihydro-isoindol-2-yl)-N-thiazol-2-yl-propionamide (outlined in Example 9, Step B) provided after flash chromatography (Merck Silica gel 60, 230–400 mesh, eluent: 50% ethyl acetate/hexanes) 161 mg (96%) of (S)-N-Benzdoxazol-2-yl-3-cyclohexyl-2-(1-oxo-1,3-dihydro-isoindol-2-yl)-propionamide as a white foam: EI-HRMS m/e calcd for $C_{24}H_{25}N_3O_3$ (M$^+$) 403.1896, found 403.1895.

Example 17

3-Cyclopentyl-2-(1-oxo-1,3-dihydro-isoindol-2-yl)-N-thiazol-2-yl-propionamide

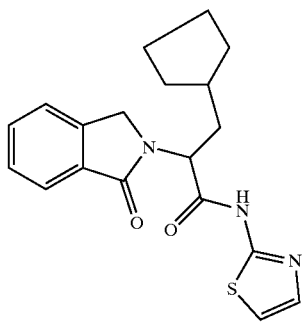

Step A: 3-Cyclopentyl-2-(1-oxo-1,3-dihydro-isoindol-2-yl)-propionic Acid

A mixture of 2-Amino-3-cyclopentyl-propionic acid (0.800 g; 5.09 mmol) and phthalic dicarboxaldehyde (0.684 g; 5.10 mmol) in acetonitrile (30 mL) was refluxed for 3 h under nitrogen. The mixture was allowed to cool to room temperature and the solid was filtered off and washed once with cold acetonitrile (5 mL) to give 1.16 g (83%) of 3-Cyclopentyl-2-(1-oxo-1,3-dihydro-isoindol-2-yl)-propionic acid as a white solid: EI-HRMS m/e calcd for $C_{16}H_{19}NO_3$ (M$^+$) 273.1365, found 273.1374.

Step B: 3-Cyclopentyl-2-(1-oxo-1,3-dihydro-isoindol-2-yl)-N-thiazol-2-yl-propionamide BOP coupling of (3-Cyclopentyl-2-(1-oxo-1,3-dihydro-isoindol-2-yl)-propionic acid (prepared in Step A; 273 mg; 1.00 mmol) and 2-aminothiazole (100 mg; 1.00 mmol) in a manner similar to that used for the preparation of (R)-3-cyclohexyl-2-(1-oxo-1,3-dihydro-isoindol-2-yl)-N-thiazol-2-yl-propionamide (outlined in Example 9, Step B) provided after flash chromatography (Merck Silica gel 60, 230–400 mesh, eluent: 40% ethyl acetate/hexanes) 132 mg (37%) of 3-Cyclopentyl-2-(1-oxo-1,3-dihydro-isoindol-2-yl)-N-thiazol-2-yl-propionamide as a white solid: ES-HRMS m/e calcd for $C_{19}H_{21}N_3O_2SNa$ (M$^+$+Na$^+$) 378.1247, found 378.1250.

Example 18

N-(5-Chloro-thiazol-2-yl)-3-cyclopentyl-2-(1-oxo-1,3-dihydro-isoindol-2-yl)-propionamide

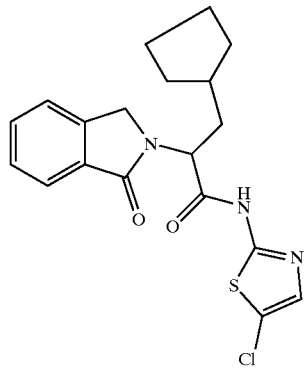

BOP coupling of 3-Cyclopentyl-2-(1-oxo-1,3-dihydro-isoindol-2-yl)-propionic acid (prepared in Example 1, Step A; 277 mg; 1.0 mmol) and 2-amino-5-chlorothiazole hydrochloride (397 mg; 2.30 mmol) in a manner similar to that used for the preparation of (S)-3-cyclohexyl-2-(1-oxo-1,3-dihydro-isoindol-2-yl)-N-thiazol-2-yl-propionamide as outlined in Example 1, Step B) provided after Flash chromatography (Biotage 40M eluent: 20% ethyl acetate/hexanes) 290 mg (74%) of N-(5-Chloro-thiazol-2-yl)-3-cyclopentyl-2-(1-oxo-1,3-dihydro-isoindol-2-yl)-propionamide as a light yellow solid: EI-HRMS m/e calcd for $C_{19}H_{21}N_3O_2S$ (M$^+$) 389.0965, found 389.0966.

Example 19

3-Cycloheptyl-2-(1-oxo-1,3-dihydro-isoindol-2-yl)-N-thiazol-2-yl-propionamide

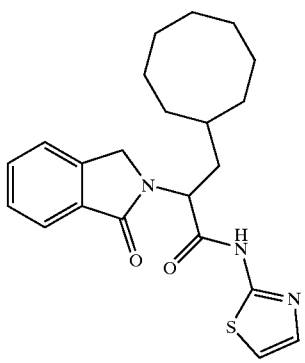

Step A: Cycloheptane Methanol

To a stirred solution of borane tetrahydrofuran complex (95 mL of 1.5 M solution in tetrahydrofuran/ether) under argon at 0° C. was added cycloheptanecarboxylic acid (10.05 g; 69.3 mmol) in 30 mL tetrahydrofuran. After 2 h, the mixture was quenched by careful addition of methanol and the mixture concentrated in vacuo. The residue was taken up into ethyl acetate and washed with successively with 1N HCl, saturated sodium bicarbonate and brine solutions. The organic layer was dried (sodium sulfate) filtered and concentrated in vacuo to give 9.19 g (100%) of cycloheptane methanol as a colorless oil.

Step B: Cycloheptylmethyl Iodide

To a stirred solution of triphenylphosphine (24.59 g; 92.8 mmol) and imidazole (6.40 g; 93.1 mmol) in methylene chloride (100 mL) cooled to 0° C. and Iodine (23.52 g; 92.7 mmol) was added portionwise over a 10 minute period. A solution of cycloheptane methanol (9.14 g; 71.3 mmol) dissolved in methylene chloride (50 mL) was then added over a 5 minute period. The cooling bath was removed and the mixture allowed to warm to room temperature and stirred overnight. The mixture was diluted with methylene chloride, washed with water and the organic layer dried (magnesium sulfate), filtered and concentrated in vacuo. The crude product was chromatographed (eluent:hexanes) to give 15.35 g (93%) of cycloheptylmethyl iodide as an oil.

Step C: 2-(Benzhydrylidene-amino)-3-cycloheptyl-propionic Acid Tert-butyl Ester To a stirred solution of (Benzhydrylidene-amino)-acetic acid tert-butyl ester (2.56 g; 8.68 mmol) in 30 mL of tetrahydrofuran under argon at −78° C. was added lithium diisopropylamide solution (10.0 mL; 1.5 M solution in cyclohexane) dropwise. After 30 minutes, a solution of cycloheptylmethyl iodide (Prepared in Step B; 3.48 g; 14.6 mmol) in 20 mL tetrahydrofuran was added dropwise and the mixture allowed to warm to room temperature and stirred for 18 h. The mixture was quenched with saturated ammonium chloride solution (100 mL). The layers were separated and the aqueous layer was extracted with ethyl acetate. The combined organic layers were dried (sodium sulfate) filtered and concentrated in vacuo. The crude product was chromatographed (Biotage 40M; eluent: 5% ethyl acetate/hexanes) to give 2.56 g (73%) of 2-(Benzhydrylidene-amino)-3-cycloheptyl-propionic acid tert-butyl ester as a pale yellow oil.

Step D: 2-Amino-3-cycloheptyl-propionic Acid

To a solution of 2-(Benzhydrylidene-amino)-3-cycloheptyl-propionic acid tert-butyl ester (1.34 g; 3.31 mmol) in methanol (5 mL) was added 10N HCl solution (15 mL) and the mixture heated to reflux. After 15 h, the mixture was allowed to cool to room temperature and transferred to a separatory funnel and washed with ethyl acetate. The aqueous layer was then neutralized with concentrated ammonium hydroxide solution and the white solid was filtered off and air dried to give 329 mg of 2-Amino-3-cycloheptyl-propionic acid.

Step E: 3-Cycloheptyl-2-(1-oxo-1,3-dihydro-isoindol-2-yl)-propionic Acid

A solution of phthalic dicarboxaldehyde (248 mg; 1.80 mmol) and 2-Amino-3-cycloheptyl-propionic acid (318 mg; 1.72 mmol) in acetonitrile was heated to reflux for 18 h. The mixture was then allowed to cool to room temperature and the mixture stored in the refrigerator for 3 h. The solid was filtered off, rinsed with cold acetonitrile and air dried to give 424 mg (82%) of 3-Cycloheptyl-2-(1-oxo-1,3-dihydro-isoindol-2-yl)-propionic acid as a beige solid: EI-HRMS m/e calcd for $C_{18}H_{23}NO_3$ (M+) 301.1678, found 301.1668.

Step F: 3-Cycloheptyl-2-(1-oxo-1,3-dihydro-isoindol-2-yl)-N-thiazol-2-yl-propionamide BOP coupling of 3-Cycloheptyl-2-(1-oxo-1,3-dihydro-isoindol-2-yl)-propionic acid (prepared in Step E; 173 mg; 0.58 mmol) and 2-aminothiazole (97 mg; 0.94 mmol) in a manner similar to that used for the preparation of (S)-3-cyclohexyl-2-(1-oxo-1,3-dihydro-isoindol-2-yl)-N-thiazol-2-yl-propionamide as outlined in Example 1, Step B) provided after flash chromatography (Biotage 40S, eluent: 35% ethyl acetate/hexanes) 217 mg (99%) of 3-Cycloheptyl-2-(1-oxo-1,3-dihydro-isoindol-2-yl)-N-thiazol-2-yl-propionamide as a white foam EI-HRMS m/e calcd for $C_{21}H_{25}N_3O_2S$ (M+) 383.1667, found 383.1660.

Example 20

N-(5-Chloro-thiazol-2-yl)-3-cycloheptyl-2-(1-oxo-1,3-dihydro-isoindol-2-yl)-propionamide

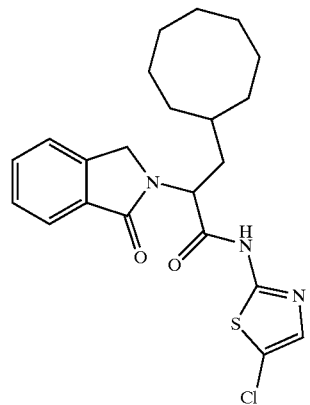

BOP coupling of 3-Cycloheptyl-2-(1-oxo-1,3-dihydro-isoindol-2-yl)-propionic acid (prepared in Step E; 177 mg; 0.59 mmol) and 2-amino-5-chlorothiazole hydrochloride (168 mg; 0.95 mmol) in a manner similar to that used for the preparation of (S)-3-cyclohexyl-2-(1-oxo-1,3-dihydro-isoindol-2-yl)-N-thiazol-2-yl-propionamide as outlined in Example 1, Step B) provided after flash chromatography (Biotage 40M, eluent: 20% ethyl acetate/hexanes) 99 mg (40%) of N-(5-Chloro-thiazol-2-yl)-3-cycloheptyl-2-(1-oxo-1,3-dihydro-isoindol-2-yl)-propionamide as an off white foam EI-HRMS m/e calcd for $C_{21}H_{24}ClN_3O_2S$ (M+) 417.1278, found 417.1289.

Example 21

3-Cyclooctyl-2-(1-oxo-1,3-dihydro-isoindol-2-yl)-N-thiazol-2-yl-propionamide

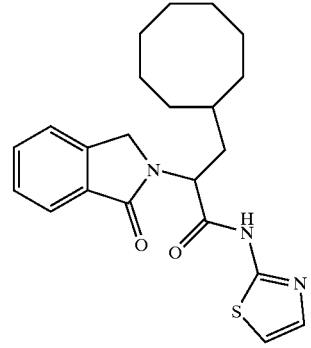

Step A: Cyclooctylmethyl Iodide

To a stirred solution of cyclooctyymethanol (5.00 g; 35.2 mmol) and Iodine (8.93 g; 35.2 mmol) in dry methylene chloride (100 mL) at room temperature was added triphenylphosphine (9.23 g; 35.2 mmol) portionwise over a 10 minute period. After 1 h, the mixture was diluted with methylene chloride, washed with water followed by saturated sodium bisulfite solution and the organic layer dried (magnesium sulfate), filtered and concentrated in vacuo. The crude product was chromatographed (eluent:hexanes) to give 5.35 g (60%) of cyclooctylmethyl iodide as an oil.

Step B: 2-(Benzhydrylidene-amino)-3-cyclooctyl-propionic Acid Tert-butyl Ester

To a stirred solution of (Benzhydrylidene-amino)-acetic acid tert-butyl ester (3.00 g; 10.1 mmol) in 60 mL of tetrahydrofuran under argon at −78° C. was added lithium diisopropylamide solution (11.5 mL; 1.5 M solution in cyclohexane) dropwise. After 30 minutes, a solution of cycloheptylmethyl iodide (Prepared in Step A; 3.83 g; 15.2 mmol) was added dropwise via syringe and the mixture allowed to warm to room temperature and stirred for 18 h. The mixture was quenched with saturated sodium bicarbonate solution and most of the tetrahydrofuran was removed in vacuo. The mixture was diluted with water and extracted with methylene chloride. The combined extracts were dried (sodium sulfate) filtered and concentrated in vacuo. The crude product was chromatographed (eluent:4% ethyl acetate/hexanes) to give 3.34 g (79%) of 2-(Benzhydrylidene-amino)-3-cyclooctyl-propionic acid tert-butyl ester as a pale yellow oil.

Step C: 2-Amino-3-cyclooctyl-propionic Acid

To a solution of 2-(Benzhydrylidene-amino)-3-cyclooctyl-propionic acid tert-butyl ester (2.00 g) in methanol (15 mL) was added 10N HCl solution (30 mL) and the mixture heated to reflux. After 20 h, the mixture was allowed to cool to room temperature, diluted with 20 mL of water, transferred to a separatory funnel and washed with ethyl acetate. The aqueous layer was then neutralized with 10N sodium hydroxide solution and further cooled to 0° C. The white solid was filtered off and air dried to give 590 mg of 2-Amino-3-cyclooctyl-propionic acid.

Step D: 3-Cyclooctyl-2-(1-oxo-1,3-dihydro-isoindol-2-yl)-propionic Acid

A solution of phthalic dicarboxaldehyde (349 mg; 2.60 mmol) and 2-Amino-3-cyclooctyl-propionic acid (500 mg; 2.51 mmol) in acetonitrile (20 mL) was heated to reflux for 3 h. The mixture was then hot filtered to remove insoluble material and then allowed to cool to room temperature and then further cooled to 0° C. The solid was filtered off, rinsed with cold acetonitrile and air dried to give 480 mg (62%) of 3-Cyclooctyl-2-(1-oxo-1,3-dihydro-isoindol-2-yl)-propionic acid as a white solid: EI-HRMS m/e calcd for $C_{19}H_{25}NO_3$ (M+) 315.1834, found 315.1840.

Step E: 3-Cyclooctyl-2-(1-oxo-1,3-dihydro-isoindol-2-yl)-N-thiazol-2-yl-propionamide BOP coupling of 3-Cyclooctyl-2-(1-oxo-1,3-dihydro-isoindol-2-yl)-propionic acid (prepared in Step D; 200 mg; 0.65 mmol) and 2-aminothiazole (70 mg; 0.70 mmol) in a manner similar to that used for the preparation of (S)-3-cyclohexyl-2-(1-oxo-1,3-dihydro-isoindol-2-yl)-N-thiazol-2-yl-propionamide as outlined in Example 9, Step B) provided after flash chromatography (eluent: 30% ethyl acetate/hexanes) 226 mg (88%) of 3-Cyclooctyl-2-(1-oxo-1,3-dihydro-isoindol-2-yl)-N-thiazol-2-yl-propionamide as a white foam: EI-HRMS m/e calcd for $C_{22}H_{27}N_3O_2S$ (M+) 397.1824, found 397.1825.

Example 22

(R)-N-(5-Bromo-pyridin-2-yl)-3-cyclohexyl-2-(1-oxo-1,3-dihydro-isoindol-2-yl)-propionamide

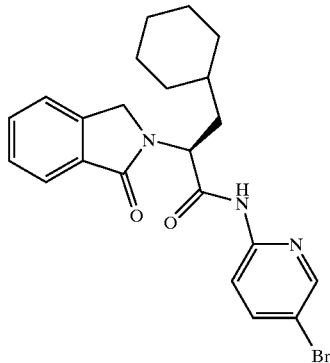

BOP coupling of (S)-3-Cyclohexyl-2-(1-oxo-1,3-dihydro-isoindol-2-yl)-propionic acid (prepared in Example 1, Step A; 287 mg; 1.00 mmol) and 2-amino-5-bromopyridine (173 mg; 1.00 mmol) in a manner similar to that used for the preparation of (R)-3-cyclohexyl-2-(1-oxo-1,3-dihydro-isoindol-2-yl)-N-thiazol-2-yl-propionamide (outlined in Example 9, Step B) provided after flash chromatography (Merck Silica gel 60, 230–400 mesh, eluent: 30% ethyl acetate/hexanes) 243 mg (55%)of (S)-N-(5-Bromo-pyridin-2-yl)-3-cyclohexyl-2-(1-oxo-1,3-dihydro-isoindol-2-yl)-propionamide as a white foam: EI-HRMS m/e calcd for $C_{22}H_{24}BrN_3O_2$ (M+) 441.1052, found 441.1036.

Example 23

23.1(S)-3-Cyclohexyl-2-(4-fluoro-1-oxo-1,3-dihydro-isoindol-2-yl)-N-thiazol-2-yl-propionamide and 23.2. (S)-3-Cyclohexyl-2-(7-fluoro-1-oxo-1,3-dihydro-isoindol-2-yl)-N-thiazol-2-yl-propionamide

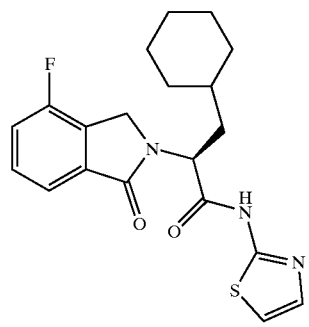

BOP coupling of (S)-3-cyclohexyl-2-(4-fluoro-1-oxo-1,3-dihydro-isoindol-2-yl)-propionic and (S)-3-cyclohexyl-2-(7-fluoro-1-oxo-1,3-dihydro-isoindol-2-yl)-propionic acid (499 mg; 1.63 mmol, as a 1:1 mixture of regioisomers) and 2-aminothiazole (376 mg; 3.64 mmol) in a manner similar to that used for the preparation of (S)-3-cyclohexyl-2-(1-oxo-1,3-dihydro-isoindol-2-yl)-N-thiazol-2-yl-propionamide (outlined in Example 9, Step B) provided after flash chromatography (Biotage 40M; eluent: 30% ethyl acetate/hexanes) (S)-3-Cyclohexyl-2-(4-fluoro-1-oxo-1,3-dihydro-isoindol-2-yl)-N-thiazol-2-yl-propionamide (221 mg): EI-HRMS calcd for $C_{20}H_{22}FN_3O_2S$ (M+) 387.1417, found 387.1422; and impure (S)-3-Cyclohexyl-2-(7-fluoro-1-oxo-1,3dihydro-isoindol-2-yl)-N-thiazol-2-yl-propionamide which was further purified by radial chromatography (eluent:35% ethyl acetate/hexanes) providing 48 mg of pure (S)-3-Cyclohexyl-2-(7-fluoro-1-oxo-1,3dihydro-isoindol-2-yl)-N-thiazol-2-yl-propionamideas a white foam: EI-HRMS m/e calcd for $C_{20}H_{22}FN_3O_2S$ (M$^+$) 387.1417, found 387.1415.

Example 24

(S)-3-Cyclohexyl-N-(1H-imidazol-2-yl)-2-(1-oxo-1,3-dihydro-isoindol-2-yl) propionamide

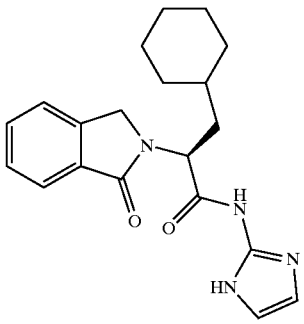

BOP coupling of (S)-3-Cyclohexyl-2-(1-oxo-1,3-dihydro-isoindol-2-yl)-propionic acid (prepared in Example 1, Step A; 287 mg; 1.00 mmol) and 2-aminoimidazole (241 mg; 1.79 mmol) in a manner similar to that used for the preparation of (S)-3-cyclohexyl-2-(1-oxo-1,3-dihydro-isoindol-2-yl)-N-thiazol-2-yl-propionamide (outlined in Example 1, Step B) provided after flash chromatography (Biotage 40M; eluent: 4% methanol/methylene chloride) 320 mg of (S)-3-Cyclohexyl-N-(1H-imidazol-2-yl)-2-(1-oxo-1,3-dihydro-isoindol-2-yl) propionamide which was then recrystallized from ethyl acetate/hexanes to give 209 mg of pure material: EI-HRMS m/e calcd for $C_{20}H_{24}N_4O_2$ (M$^+$) 352.1899, found 352.1895.

Example 25

25.1 (S)-3-Cyclohexyl-2-(4-fluoro-1-oxo-1,3dihydro-isoindol-2-yl)-N-pyrazin-2-yl-propionamide and 25.2. (S)-3-cyclohexyl-2-(7-fluoro-1-oxo-1,3-dihydro-isoindol-2-yl)-N-pyrazin-2-yl-propionamide

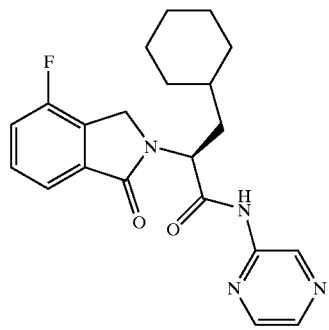

BOP coupling of (S)-3-cyclohexyl-2-(4-fluoro-1-oxo-1,3-dihydro-isoindol-2-yl)-propionic and (S)-3-cyclohexyl-2-(7-fluoro-1-oxo-1,3-dihydro-isoindol-2-yl)-propionic acid (331 mg; 1.08 mmol, as a 1:1 mixture of regioisomers) and 2-aminopyrazine (232 mg; 2.41 mmol) in a manner similar to that used for the preparation of (S)-3-cyclohexyl-2-(1-oxo-1,3-dihydro-isoindol-2-yl)-N-thiazol-2-yl-propionamide (outlined in Example 9, Step B) provided after flash chromatography (Biotage 40M; eluent: 30% ethyl acetate/hexanes) (S)-3-Cyclohexyl-2-(4-fluoro-1-oxo-1,3-dihydro-isoindol-2-yl)-N-thiazol-2-yl-propionamide and (S)-3-Cyclohexyl-2-(7-fluoro-1-oxo-1,3 dihydro-isoindol-2-yl)-N-thiazol-2-yl-propionamide which were further purified by reverse phase HPLC (Rainin Dynamax SD-1 instrument) using a gradient of 40% acetonitrile/water/0.1% trifluoroacetic acid to 100% acetonitrile on a C18 column to provide 39 mg of pure (S)-3-Cyclohexyl-2-(7-fluoro-1-oxo-1,3dihydro-isoindol-2-yl)-N-thiazol-2-yl-propionamide as a white foam: EI-HRMS m/e calcd for $C_{21}H_{23}FN_4O_2$ (M$^+$) 382.1805, found 382.1794 and 43 mg of regioisomer (S)-3-Cyclohexyl-2-(7-fluoro-1-oxo-1,3-dihydro-isoindol-2-yl)-N-thiazol-2-yl-propionamide: EI-HRMS m/e calcd for $C_{21}H_{23}FN_4O_2$ (M$^+$) 382.1805, found 382.1810.

Example 26

(S)3-Cyclohexyl-2-(1-oxo-1,3-dihydro-isoindol-2-yl)-N-pyridin-2-yl-propionamide

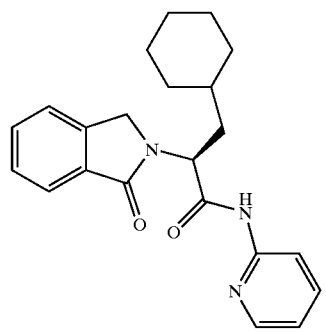

BOP coupling of (S)-3-Cyclohexyl-2-(1-oxo-1,3-dihydro-isoindol-2-yl)-propionic acid (prepared in Example 1, Step A; 287 mg; 1.00 mmol) and 2-aminopyridine (94 mg; 1.00 mmol) in a manner similar to that used for the preparation of (R)-3-cyclohexyl-2-(1-oxo-1,3-dihydro-isoindol-2-yl)-N-thiazol-2-yl-propionamide (outlined in Example 9, Step B) provided after flash chromatography (Merck Silica gel 60, 230–400 mesh, eluent: 45% ethyl acetate/hexanes) 186 mg of (S)-3-Cyclohexyl-2-(1-oxo-1,3-dihydro-isoindol-2-yl)-N-pyridin-2-yl-propionamide as a white foam: EI-HRMS m/e calcd for $C_{22}H_{25}N_3O_2$ (M$^+$) 363.1947, found 363.1935.

Example 27

(S)-N-3-Cyclohexyl-N-(2-methyl-pyrimidin-4-yl)-2-(1-oxo-1,3-dihydro-isoindol-2-yl)-propionamide

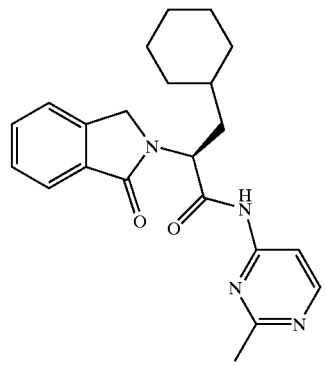

BOP coupling of (S)-3-Cyclohexyl-2-(1-oxo-1,3-dihydro-isoindol-2-yl)-propionic acid (prepared in Example 1, Step A; 150 mg; 0.52 mmol) and 2-amino-6-methylpyrimidine (57 mg; 0.52 mmol) in a manner similato that used for the preparation of (R)-3-cyclohexyl-2-(1-oxo-1,3-dihydro-isoindol-2-yl)-N-thiazol-2-yl-propionamide (outlined in Example 9, Step B) provided after flash chromatography (Merck Silica gel 60, 230–400 mesh, eluent: 65% ethyl acetate/hexanes) 109 mg of (S)-3-Cyclohexyl-N-(2-methyl-pyrimidin-4-yl)-2-(1-oxo-1,3-dihydro-isoindol-2-yl)-propionamide as a white foam: EI-HRMS m/e calcd for $C_{22}H_{26}N_4O_2$ ($M^+$) 378.2056, found 378.2054.

Example 28

28.1 (S)-3-Cyclohexyl-2-(4-methylsulfonyl-1-oxo-1,3dihydro-isoindol-2-yl)-N-thiazol-2-yl-propionamide and 28.2. (S)-3-cyclohexyl-2-(7-methylsulfonyl-1-oxo-1,3-dihydro-isoindol-2-yl)-propionamide

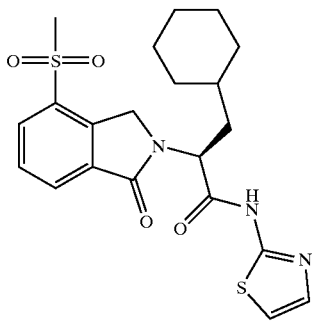

Step A: 3-fluorophthalic Acid, Dimethyl Ester

Hydrochloric acid was bubbled into a stirred solution of 3-fluorophthalic acid (2.00 g; 10.9 mmol) in dry methanol at room temperature for 2 minutes. The mixture was warmed to reflux. After 1 h at at reflux, 1 mL of concentrated sulfuric acid was added and reflux continued for 22 h. The mixture was allowed to cool to room temperature and then neutralized with saturated sodium bicarbonate solution. The resulting mixture was extracted with ethyl acetate. The extracts were dried (sodium sulfate), filtered and concentrated in vacuo to give 1.70 g of 3-fluorophthalic acid, dimethyl ester as an oil.

Step B: 3thiomethylphthalic Acid

A mixture of 3-fluorophthalic acid, dimethyl ester (2.27 g; 10.7 mmol) and sodium thiomethoxide (6.34 g; 85.9 mmol) in DMSO (20 mL) was heated to 5° C. After 24 h, crushed ice was added and the resulting mixture acidified with 1N HCl. The solution was extracted with ethyl acetate and the extracts were washed with brine, dried (sodium sulfate), filtered and concentrated in vacuo. The crude product was purified by reverse phase HPLC (Rainin Dynamax SD-1 instrument) using a gradient of 0% acetonitrile/water/0.1% trifluoroacetic acid to 100% acetonitrile on a C18 column to provide 802 mg of 3-thiomethylphthalic acid.

Step C: 3-thiomethyl-1,2-di-(hydroxymethyl) benzene

To a stirred solution of borane.tetrahydrofuran complex (14.0 mL of 1.5 M solution in tetrahydrofuran/diethyl ether) cooled to 0° C. under argon was added a solution of 3-thiomethylphthalic acid (0.739 g; 3.48 mmol) in 20 mL tetrahydrofuran. At the end of the addition, the mixture was refluxed for 15 h. The mixture was allowed to cool to room temperature, quenched with methanol (20 mL), refluxed for 2 h and concentrated in vacuo. The residue was partitioned between 1N HCl and ethyl acetate. The aqueous layer was further extracted with ethyl acetate and the combined extracts were washed saturated sodium bicarbonate, brine and dried (sodium sulfate), filtered and concentrated in vacuo to give crude 3-thiomethyl-1,2-di-(hydroxymethyl) benzene which was purified flash chromatography (Biotage 40M; eluent: 25%–50% gradient of ethyl acetate/hexanes) to give 454 mg of pure 3-thiomethyl-1,2-di-(hydroxymethyl) benzene.

Step D: 3-thiomethylphthalic Dicarboxaldehyde

To a stirred solution of oxalyl chloride (0.42 mL; 4.72 mmol) in anhydrous methylene chloride (5 mL) under argon at −78° C. was added a solution of dimethyl sulfoxide (0.70 mL; 9.67 mmol) in methylene chloride (2 mL) dropwise. The solution was stirred for 10 minutes and then a solution of 3-thiomethyl-1,2-di-(hydroxymethyl) benzene (0.415 g; 2.25 mmol) dissolved in 3 mL of 1:1 methylene chloride/dimethyl sulfoxide was added dropwise. The resulting mixture was stirred at −78° C. for 2 h. Triethylamine (5.5 mL; 17.4 mmol) was added dropwise and then the mixture allowed to gradually warm to room temperature and stirred for 20 h. The mixture was poured into ice water the layers were separated. The extract was washed with brine and then dried (sodium sulfate) and concentrated to give crude 3-thiomethylphthalic dicarboxaldehyde which was not further purified.

Step E: (S)-3-cyclohexyl-2-(4-methylthio-1-oxo-1, 3-dihydro-isoindol-2-yl)-propionic Acid A mixture of (S)-(+)-α-aminocyclohexanepropionic acid hydrate (0.125 g; 0.70 mmol) and crude 3-thiomethylphthalic dicarboxaldehyde (prepared in StepD; 0.250 g; 1.4 mmol) in acetonitrile (5 mL) was heated to reflux under argon for 18 h. The mixture was allowed to cool to room temperature and concentrated in vacuo. The crude product was purified by flash chromatography (Biotage 40S; eluent: 5% methanol/methylene chloride) to give 260 mg of (S)-3-cyclohexyl-2-(4-methylthio-1-oxo-1,3-dihydro-isoindol-2-yl)-propionic acid together with regio-isomeric (S)-3-cyclohexyl-2-(7-methylthio-1-oxo-1,3-dihydro-isoindol-2-yl)-propionic acid in a ratio of about 1:1.

Step F: (S)-3-cyclohexyl-2-(4-methylsulfonyl-1-oxo-1,3-dihydro-isoindol-2-yl)-propionic Acid To a solution of (S)-3-cyclohexyl-2-(4-methylthio-1-oxo-1,3-dihydro-isoindol-2-yl)-propionic acid and regio-isomeric(S)-3-cyclohexyl-2-(7-methylthio-1-oxo-1,3-dihydro-isoindol-2-yl)-propionic acid (0.790 g; 2.37 mmol; ca. 1:1 mixture) in formic acid (4mL) at 0° C. was added 30% hydrogen peroxide solution (1.3 mL; 12.7 mmol) dropwise. The mixture was allowed to warm to room temperature and stirred for 19 h. The mixture was concentrated under a stream of nitrogen to remove the formic acid to give 0.901 g of crude (S)-3-cyclohexyl-2-(4-methylsulfonyl-1-oxo-1,3-dihydro-isoindol-2-yl)-propionic acid and regio-isomeric (S)-3-cyclohexyl-2-(7-methylsulfonyl-1-oxo-1,3-dihydro-isoindol-2-yl)-propionic acid.

Step G: (S)-3-Cyclohexyl-2-(7-methylsulfonyl-1-oxo-1,3dihydro-isoindol-2-yl)-N-thiazol-2-yl-propionamide BOP coupling of (S)-3-cyclohexyl-2-(4-methylsulfonyl-1-oxo-1,3-dihydro-isoindol-2-yl)-propionic acid and regioisomeric (S)-3-cyclohexyl-2-(7-methylsulfonyl-1-oxo-1,3-dihydro-isoindol-2-yl)-propionic acid (112 mg; 0.31 mmol) and 2-aminothiazole (54 mg; 0.52 mmol) in a manner similar to that used for the preparation of (S)-3-cyclohexyl-2-(1-oxo-1,3-dihydro-isoindol-2-yl)-N-thiazol-2-yl-propionamide (outlined in Example 9, Step B) provided after flash chromatography (Biotage 40M; eluent: ethyl acetate/methylene chloride: gradient 15%–50% ethyl acetate) provided 51 mg (S)-3-Cyclohexyl-2-(4-methylsulfonyl-1-oxo-1,3dihydro-isoindol-2-yl)-N-thiazol-2-yl-propionamide: EI-HRMS m/e calcd for $C_{21}H_{25}N_3O_4S_2$ $(M^{+-2})$ 445.1130, found 445.1125 and 39 mg of (S)-3-Cyclohexyl-2-(7-methylsulfonyl-1-oxo-1,3dihydro-isoindol-2-yl)-N-thiazol-2-yl-propionamide: EI-HRMS m/e calcd for $C_{21}H_{25}N_3O_4S_2$ $(M^+)$ 447.1286, found 447.1280.

Example 29

29.1 (S)-3-Cyclohexyl-2-(4-methylsulfonyl-1-oxo-1,3dihydro-isoindol-2-yl)-N-pyrazin-2-yl-propionamide and 29.2. (S)-3-cyclohexyl-2-(7-methylsulfonyl-1-oxo-1,3-dihydro-isoindol-2-yl)-N-pyrazin-2-yl-propionamide

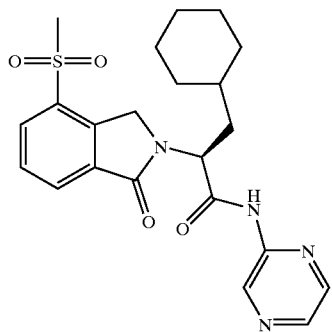

BOP coupling of (S)-3-cyclohexyl-2-(4-methylsulfonyl-1-oxo-1,3-dihydro-isoindol-2-yl)-propionic acid and regioisomeric (S)-3-cyclohexyl-2-(7-methylsulfonyl-1-oxo-1,3-dihydro-isoindol-2-yl)-propionic acid (200 mg; 0.55 mmol) and 2-aminopyrazine (88 mg; 0.91 mmol) in a manner similar to that used for the preparation of (S)-3-cyclohexyl-2-(1-oxo-1,3-dihydro-isoindol-2-yl)-N-thiazol-2-yl-propionamide (outlined in Example 9, Step B) provided after flash chromatography (Biotage 40S; eluent: ethyl acetate/methylene chloride, gradient:20% to 60%) a crude mixture that was further purified by reverse phase HPLC (Rainin Dynamax SD-1 instrument) using a gradient of 10% acetonitrile/water/0.1% trifluoroacetic acid to 90% acetonitrile on a $C_{18}$ column to give 21 mg of (S)-3-Cyclohexyl-2-(4-methylsulfonyl-1-oxo-1,3-dihydro-isoindol-2-yl)-N-pyrazin-2-yl-propionamide: EI-HRMS m/e calcd for $C_{22}H_{24}N_4O_4SNa$ $(M^++Na^+)$ 465.1567, found 465.1570 and 13 mg of (S)-3-Cyclohexyl-2-(7-methylsulfonyl-1-oxo-1,3-dihydro-isoindol-2-yl)-N-pyrazin-2-yl-propionamide: EI-HRMS m/e calcd for $C_{22}H_{24}N_4O_4SNa$ $(M^++Na^+)$ 465.1567, found 465.1568.

Example 30

30.1(S)-3-Cyclohexyl-2-(4-methylsulfonyl-1-oxo-1,3-dihydro-isoindol-2-yl)-N-pyrimidin-4-yl-propionamide and 30.2.(S)-3-Cyclohexyl-2-(7-methylsulfonyl-1-oxo-1,3-dihydro-isoindol-2-yl)-N-pyrimidin-4-yl-propionamide

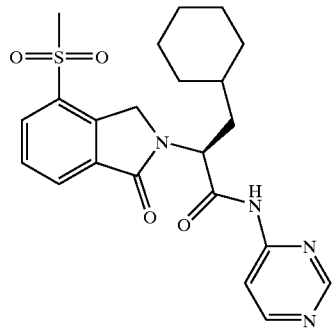

BOP coupling of (S)-3-cyclohexyl-2-(4-methylsulfonyl-1-oxo-1,3-dihydro-isoindol-2-yl)-propionic acid and regioisomeric (S)-3-cyclohexyl-2-(7-methylsulfonyl-1-oxo-1,3-dihydro-isoindol-2-yl)-propionic acid (200 mg; 0.55 mmol) and 4-aminopyrimidine (89 mg; 0.91 mmol) in a manner similar to that used for the preparation of (S)-3-cyclohexyl-2-(1-oxo-1,3-dihydro-isoindol-2-yl)-N-thiazol-2-yl-propionamide (outlined in Example 9, Step B) provided after flash chromatography (Biotage 40S; eluent: ethyl acetate/methylene chloride, gradient: 25% to 70% ethyl acetate) to give 83 mg of (S)-3-Cyclohexyl-2-(4-methylsulfonyl-1-oxo-1,3-dihydro-isoindol-2-yl)-N-pyrimidin-4-yl-propionamide as a foam: EI-HRMS m/e calcd for $C_{22}H_{24}N_4O_4SNa$ $(M^++Na^+)$ 465.1567, found 465.1568 and 77 mg (S)-3-Cyclohexyl-2-(7-methylsulfonyl-1-oxo-1,3-dihydro-isoindol-2-yl)-N-pyrimidin-4-yl-propionamide as a foam: EI-HRMS m/e calcd for $C_{22}H_{26}N_4O_4SNa$ $(M^++Na^+)$ 465.1567, found 465.1572.

Example 31

(S)-3-Cyclohexyl-2-(1-oxo-1,3-dihydro-isoindol-2-yl)-N-5-methyl-pyridin-2-yl-propionamide

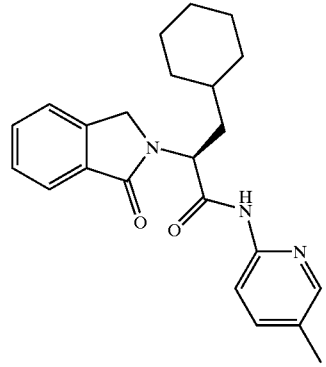

BOP coupling of (S)-3-Cyclohexyl-2-(1-oxo-1,3-dihydro-isoindol-2-yl)-propionic acid (prepared in Example 1, Step A; 287 mg; 1.00 mmol) and 2-amino-5-methylpyridine (143 mg; 1.32 mmol) in a manner similar to that used for the preparation of (S)-3-cyclohexyl-2-(1-oxo-1,3-dihydro-isoindol-2-yl)-N-thiazol-2-yl-propionamide (outlined in Example 1, Step B) provided after flash chromatography (Biotage 40S; eluent: 30% ethyl acetate/hexanes) 352 mg of (S)-3-Cyclohexyl-2-(1-oxo-1,3-dihydro-isoindol-2-yl)-N-5-methyl-pyridin-2-yl-propionamide as a white foam: EI-HRMS m/e calcd for $C_{23}H_{27}N_3O_2$ (M$^+$) 377.2103, found 377.2107.

Example 32

(S)-3-Cyclohexyl-2-(1-oxo-1,3-dihydro-isoindol-2-yl)-N-4-methyl-pyridin-2-yl-propionamide

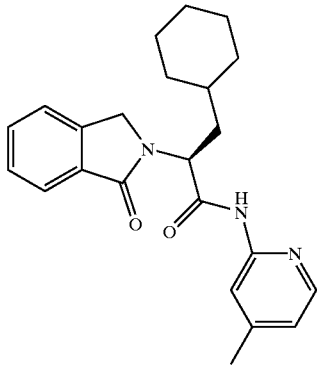

BOP coupling of (S)-3-Cyclohexyl-2-(1-oxo-1,3-dihydro-isoindol-2-yl)-propionic acid (prepared in Example 1, Step A; 287 mg; 1.00 mmol) and 2-amino-4-methylpyridine (143 mg; 1.32 mmol) in a manner similar to that used for the preparation of (S)-3-cyclohexyl-2-(1-oxo-1,3-dihydro-isoindol-2-yl)-N-thiazol-2-yl-propionamide (outlined in Example 1, Step B) provided after flash chromatography (Biotage 40S; eluent: 30% ethyl acetate/hexanes) 344 mg of (S)-3-Cyclohexyl-2-(1-oxo-1,3-dihydro-isoindol-2-yl)-N-4-methyl-pyridin-2-yl-propionamide as a white foam: EI-HRMS m/e calcd for $C_{23}H_{27}N_3O_2$ (M$^+$) 377.2103, found 377.2106.

Example 33

(S)-3-Cyclohexyl-2-(1-oxo-1,3-dihydro-isoindol-2-yl)-N-5-chloro-pyridin-2-yl-propionamide

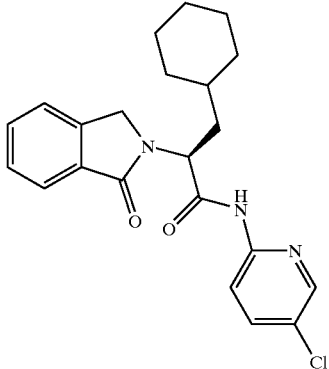

BOP coupling of (S)-3-Cyclohexyl-2-(1-oxo-1,3-dihydro-isoindol-2-yl)-propionic acid (prepared in Example 1, Step A; 287 mg; 1.00 mmol) and 2-amino-5-chloropyridine (129 mg; 1.00 mmol) in a manner similar to that used for the preparation of (S)-3-cyclohexyl-2-(1-oxo-1,3-dihydro-isoindol-2-yl)-N-thiazol-2-yl-propionamide (outlined in Example 1, Step B) provided after flash chromatography (eluent: 25% ethyl acetate/hexanes) 160 mg of (S)-3-Cyclohexyl-2-(1-oxo-1,3-dihydro-isoindol-2-yl)-N-5-chloro-pyridin-2-yl-propionamide as a white foam: EI-HRMS m/e calcd for $C_{22}H_{24}N_3O_2ClNa$(M$^+$+Na$^+$) 420.1449, found 420.1451.

Example 34

(S)-3-Cyclohexyl-2-(1-oxo-1,3-dihydro-isoindol-2-yl)-N-(1-oxy-pyridin-2-yl)-propionamide

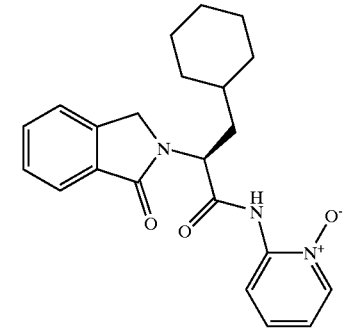

BOP coupling of (S)-3-Cyclohexyl-2-(1-oxo-1,3-dihydro-isoindol-2-yl)-propionic acid (prepared in Example 1, Step A; 287 mg; 1.00 mmol) and 2-aminopyridine N-Oxide (110 mg; 1.00 mmol) in a manner similar to that used for the preparation of (R)-3-cyclohexyl-2-( 1-oxo-1,3-dihydro-isoindol-2-yl)-N-thiazol-2-yl-propionamide (outlined in Example 9, Step B) provided after flash chromatography (Merck Silica gel 60, 230–400 mesh, eluent: 2% methanol/ethyl acetate) 340 mg (55%)of (S)-N-(pyridin-N-oxide-2-yl)-3-cyclohexyl-2-( 1-oxo-1,3-dihydro-isoindol-2-yl)-propionamide as an off white foam. The product did not appear to be pure by NMR and so it was further purified by reverse phase HPLC (Rainin Dynamax SD-1instrument) using a gradient of 10% acetonitrile/water/0.1% trifluoroacetic acid to 100% acetonitrile on a C18 column to provide 188 mg of pure (S-3-Cyclohexyl-2-(1-oxo-1,3-dihydro-isoindol-2-yl)-N-(1-oxy-pyridin-2-yl)-propionamide: ES-LRMS m/e calcd for $C_{22}H_{25}N_3O_3$ (M$^+$+H$^+$) 380, found 380.

Example 35

(S)-3-Cyclohexyl-2-(4-fluoro-1-oxo-1,3-dihydro-isoindol-2-yl)-N-pyridin-2-yl-propionamide and (S)-3-Cyclohexyl-2-(7-fluoro-1-oxo-1,3-dihydro-isoindol-2-yl)-N-pyrimidin-2-yl-propionamide

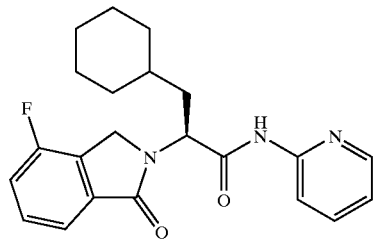

BOP coupling of (S)-3-cyclohexyl-2-(4-fluoro-1-oxo-1,3-dihydro-isoindol-2-yl)-propionic acid (ca. 1:1 mixture of regioisomers, prepared in Example 13, Step C; 501 mg; 1.64 mmol) and 2-aminopyridine (643 mg; 3.64 mmol) in a manner similar to that used for the preparation of (S)-3-cyclohexyl-2-(1-oxo-1,3-dihydro-isoindol-2-yl)-N-thiazol-2-yl-propionamide as outlined in Example 9, Step B) provided after reverse phase HPLC (Rainin Dynamax SD-1 instrument) using a gradient of 40% acetonitrile/water/0.1% trifluoroacetic acid to 70% acetonitrile on a $C_{18}$ column to give 157 mg of (S)-3-Cyclohexyl-2-(4-fluoro-1-oxo-1,3-dihydro-isoindol-2-yl)-N-4 pyridin-2-yl-propionamide: EI-HRMS m/e calcd for $C_{22}H_{24}FN_3O_2Na$ ($M^++Na^+$) 404.1745, found 404.1748; and 99 mg of regioisomeric (S)-3-Cyclohexyl-2-(7-fluoro-1-oxo-1,3-dihydro-isoindol-2-yl)-N-pyridin-2-yl-propionamide: EI-HRMS m/e calcd for $C_{22}H_{24}FN_3O_2Na$ ($M^++Na^+$) 404.1745, found 404.1749.

Example 36

(S)-3-Cyclohexyl-2-(4-Chloro-1-oxo-1,3-dihydro-isoindol-2-yl)-N-thiazol-2-yl-propionamide and (S)-3-Cyclohexyl-2-(7-Chloro-1-oxo-1,3-dihydro-isoindol-2-yl)-N-thiazol-2-yl-propionamide

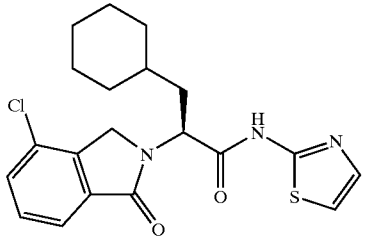

Step A: 3-chloro-1,2-di-(hydroxymethyl) benzene 3-chloro-1,2-di-(hydroxymethyl) benzene was prepared in 97% yield via borane reduction of 3-Chlorophthalic acid in a manner similar to that was used for the preparation of 3-fluoro-1,2-di-(hydroxymethyl) benzene as described in Example 13, Step A. 3-Chlorophthalic acid was prepared from according to the literature procedure of Fertel, L. B. et al. *J. Org. Chem.* 1993, 58(1), 261–263.

Step B: 3-chlorophthalic Dicarboxaldehyde 3-chlorophthalic dicarboxaldehyde was prepared via oxidation of 3-chloro-1,2-di-(hydroxymethyl) benzene (prepared in Step A) in a manner similar to that used for the preparation of 3-fluorophthalic dicarboxaldehyde as described in Example 13, Step B and the crude product was used without further purification for the next step.

Step C:(S)-3-cyclohexyl-2-(4-Chloro-1-oxo-1,3-dihydro-isoindol-2-yl)-propionic Acid and :(S)-3-cyclohexyl-2-(7-Chloro-1-oxo-1,3-dihydro-isoindol-2-yl)-propionic acid (S)-3-cyclohexyl-2-(4-Chloro-1-oxo-1,3-dihydro-isoindol-2-yl)-propionic Acid and (S)-3-cyclohexyl-2-(7-Chloro-1-oxo-1,3-dihydro-isoindol-2-yl)-propionic acid (approx. 1:1 mixture) were prepared by condensation of (S)-(+)-α-aminocyclohexanepropionic acid hydrate with 3-chlorophthalic dicarboxaldehyde (prepared in Step B) in a manner similar to that used for the preparation of (S)-3-cyclohexyl-2-(4-Fluoro-1-oxo-1,3-dihydro-isoindol-2-yl)-propionic acid and (S)-3-cyclohexyl-2-(7-Fluoro-1-oxo-1,3-dihydro-isoindol-2-yl)-propionic acid as described in Example 13, Step C.

Step D: (S)-3-Cyclohexyl-2-(4-Chloro-1-oxo-1,3-dihydro-isoindol-2-yl)-N-thiazol-2-yl-propionamide and (S)-3-Cyclohexyl-2-(7-Chloro-1-oxo-1,3dihydro-isoindol-2-yl)-N-thiazol-2-yl-propionamide BOP coupling of (S)-3-cyclohexyl-2-(4-Chloro-1-oxo-1,3-dihydro-isoindol-2-yl)-propionic acid (ca. 1:1 mixture of regioisomers, prepared in Step C; 326 mg; 1.0 mmol) and 2-aminothiazole (231 mg; 2.23 mmol) in a manner similar to that used for the preparation of (S)-3-cyclohexyl-2-(1-oxo-1,3-dihydro-isoindol-2-yl)-N-thiazol-2-yl-propionamide as outlined in Example 9, Step B) provided after chromatography (Biotage 40M column, eluent: 5% to 30% gradient of ethyl acetate/hexanes) 132 mg of (S)-3-Cyclohexyl-2-(4-Chloro-1-oxo-1,3-dihydro-isoindol-2-yl)-N-thiazol-2-yl-propionamide: EI-HRMS m/e calcd for $C_{20}H_{22}ClN_3O_2S$ ($M^++Na^+$) 426.1013, found 426.1016; and 91 mg of regioisomeric (S)-3-Cyclohexyl-2-(7-Chloro-1-oxo-1,3dihydro-isoindol-2-yl)-N-thiazol-2-yl-propionamide: EI-HRMS m/e calcd for $C_{20}H_{22}ClN_3O_2SNa$ ($M^++Na^+$) 426.1013, found 426.1017.

Example 37

(S)-N-(5-Chloro-thiazol-2-yl)-3-cyclohexyl-2-(4-Chloro-1-oxo-1,3-dihydro-isoindol-2-yl)-propionamide and (S)-N-(5-Chloro-thiazol-2-yl)-3-cyclohexyl-2-(7-Chloro-1-oxo-1,3-dihydro-isoindol-2-yl)-propionamide

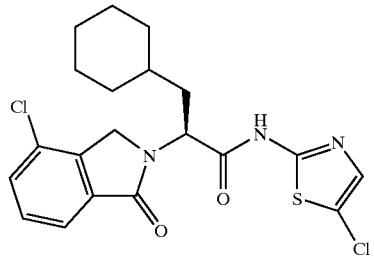

BOP coupling of (S)-3-cyclohexyl-2-(4-Chloro-1-oxo-1,3-dihydro-isoindol-2-yl)-propionic acid (ca. 1:1 mixture of regioisomers, prepared in Example 36, Step C; 151 mg; 0.47 mmol) and 2-amino-5-chlorothiazole hydrochloride(186 mg; 1.05 mmol) in a manner similar to that used for the preparation of (S)-3-cyclohexyl-2-(1-oxo-1,3-dihydro-isoindol-2-yl)-N-thiazol-2-yl-propionamide as outlined in Example 9, Step B) provided after chromatography (Biotage 40M column, eluent: 5% to 20% gradient of ethyl acetate/hexanes) 67 mg of (S)-N-(5-Chloro-thiazol-2-yl)-3-cyclohexyl-2-(4-Chloro-1-oxo-1,3-dihydro-isoindol-2-yl)-propionamide: EI-HRMS m/e calcd for $C_{20}H_{21}Cl_2N_3O_2S$ ($M^+$) 437.0731, found 437.0727; and 46 mg of regioisomeric S)-N-(5-Chloro-thiazol-2-yl)-3-cyclohexyl-2-(7-Chloro-1-oxo-1,3-dihydro-isoindol-2-yl)-propionamide: EI-HRMS m/e calcd for $C_{20}H_{21}Cl_2N_3O_2S$ ($M^++Na^+$) 437.0731, found 437.0726.

Example 38

(S)-3-Cyclohexyl-2-(4-Chloro-1-oxo-1,3-dihydro-isoindol-2-yl)-N-pyridine-2-yl-propionamide and (S)-3-Cyclohexyl-2-(7-Chloro-1-oxo-1,3-dihydro-isoindol-2-yl)-N-pyridin-2-yl-propionamide

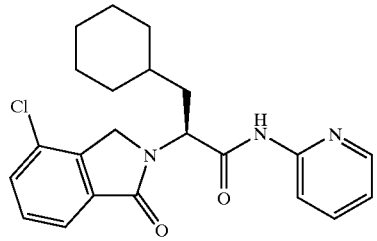

BOP coupling of (S)-3-cyclohexyl-2-(4-Chloro-1-oxo-1,3-dihydro-isoindol-2-yl)-propionic acid (ca. 1:1 mixture of regioisomers, prepared in Example 36, Step C; 201 mg; 0.62 mmol) and 2-aminopyridine(132 mg; 1.39 mmol) in a manner similar to that used for the preparation of (S)-3-cyclohexyl-2-(1-oxo-1,3-dihydro-isoindol-2-yl)-N-thiazol-2-yl-propionamide as outlined in Example 9, Step B) provided after chromatography (Biotage 40S column, eluent: 30% ethyl acetate/hexanes) 107 mg of (S)-3-Cyclohexyl-2-(4-Chloro-1-oxo-1,3-dihydro-isoindol-2-yl)-N-pyridin-2-yl-propionamide: EI-HRMS m/e calcd for $C_{22}H_{24}ClN_3O_2$ (M$^+$) 397.1557, found 397.1563; and 46 mg of regioisomeric (S)-3-Cyclohexyl-2-(7-Chloro-1-oxo-1,3dihydro-isoindol-2-yl)-N-pyridin-2-yl-propionamide: EI-HRMS m/e calcd for $C_{22}H_{24}ClN_3O_2$ (M$^+$) 397.1557, found 397.1551.

Example 39

(S)-3-Cyclohexyl-2-(4-chloro-1-oxo-1,3-dihydro-isoindol-2-yl)-N-pyrzin-2-yl-propionamide and (S)-3-Cyclohexyl-2-(4-chloro-1-oxo-1,3-dihydro-isoindol-2-yl)-N-pyrazin-2-yl-propionamide

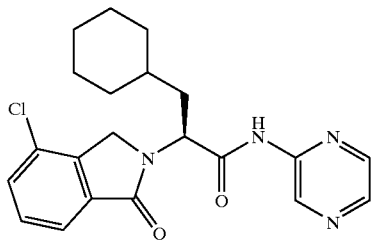

BOP coupling of (S)-3-cyclohexyl-2-(4-Chloro-1-oxo-1,3-dihydro-isoindol-2-yl)-propionic acid (ca. 1:1 mixture of regioisomers, prepared in Example 36, Step C; 243 mg; 0.76 mmol) and 2-aminopyrazine(1 70 mg; 1.77 mmol) in a manner similar to that used for the preparation of (S)-3-cyclohexyl-2-(1-oxo-1,3-dihydro-isoindol-2-yl)-N-thiazol-2-yl-propionamide as outlined in Example 9, Step B) provided after chromatography (Biotage 40M column, eluent: 20% ethyl acetate/hexanes) 53 mg of (S)-3-Cyclohexyl-2-(4-Chloro-1-oxo-1,3-dihydro-isoindol-2-yl)-N-pyrazin-2-yl-propionamide: EI-HRMS m/e calcd for $C_{21}H_{23}ClN_4O_2$ (M$^+$) 398.1510, found 398.1520; and 41 mg of regioisomeric (S)-3-Cyclohexyl-2-(7-Chloro-1-oxo-1,3dihydro-isoindol-2-yl)-N-pyrazin-2-yl-propionamide: EI-HRMS m/e calcd for $C_{21}H_{23}ClN_4O_2$ (M$^+$) 398.1510, found 398.1507.

Biological Activity Examples

All of the compounds of this invention which include the compounds set forth in the Examples activated glucokinase in vitro by the procedure of Example A. In this manner, they increase the flux of glucose metabolism which causes increased insulin secretion. Therefore, the compounds of formula I are glucokinase activators useful for increasing insulin secretion.

Example A

In Vitro Glucokinase Activity

Glucokinase Assay: Glucokinase (GK) was assayed by coupling the production of glucose-6-phosphate to the generation of NADH with glucose-6-phosphate dehydrogenase (G6PDH, 0.75-1 kunits/mg; Boehringer Mannheim, Indianapolis, Ind.) from Leuconostoc mesenteroides as the coupling enzyme (Scheme 2). Recombinant Scheme 2

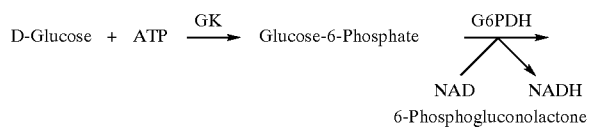

Human liver GK1 was expressed in E. coli as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 µl. The incubation mixture contained: 25 mM Hepes buffer (pH, 7.1), 25 mM KCl, 5 mM D-glucose, 1 mM ATP, 1.8 mM NAD, 2 mM $MgCl_2$, 1 µM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes that were from Sigma Chemical Co, St Louis, Mo. Test compounds were dissolved in DMSO and were added to the incubation mixture minus GST-GK in a volume of 12 µl to yield a final DMSO concentration of 10%. This mix was preincubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 µl GST-GK.

After addition of enzyme, the increase in optical density (OD) at 340 nm was monitored over a 10 minute incubation period as a measure of GK activity. Sufficient GST-GK was added to produce an increase in $OD_{340}$ of 0.08 to 0.1 units over the 10 minute incubation period in wells containing 10% DMSO, but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the $SC_{1.5}$, was calculated.

All of the compounds of this invention described in the Synthesis Examples had an $SC_{1.5}$, less than 30 µM with the exception of Example 9, which had an $SC_{1.5}$ of 36 µM. These results indicate GK activator activity.

REFERENCES FOR EXAMPLE A

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. Biochem. J. 309: 167–173, 1995.

Neet, K., Keenan, R. P., and Tippett, P. S. Observation of a kinetic slow transition in monomeric glucokinase. Biochemistry 29;770–777, 1990.

Example B:

In Vivo Activity

Glucokinase Activator in vivo Screen Protocol: C57BL/6J mice are orally dosed via gavage with Glucokinase (GK)

activator at 50 mg/kg body weight following a two hour fasting period. Blood glucose determinations are made five times during the six hour post-dose study period.

Mice (n=6) are weighed and fasted for a two hour period prior to oral treatment. GK activators are formulated at 6.76 mg/ml in Gelucire vehicle (Ethanol:Gelucire44/14:PEG400q.s. 4:66:30 v/w/v. Mice are dosed orally with 7.5 μl formulation per gram of body weight to equal to a 50 mg/kg dose. Immediately prior to dosing, a pre dose (time zero) blood glucose reading is acquired by snipping off a small portion of the animals tail (~1 mm) and collecting 15 μl blood into a heparinized capillary tube for analysis. Following GK activator administration, additional blood glucose reading are takenat 1, 2, 4 and 6 hours post dose from the same tail wound. Results are interpreted by comparing the mean blood glucose values of six vehicle treated mice with six GK activator treated mice over the six hour study duration. Compounds are considered active when they exibit a statistically significant (p ≦0.05) decrease in blood glucose compared to vehicle for two consecutive assay time points.

The compounds of Examples 1, 18, 22, 23.1, 25.1, 26, 14, 15, 31, 33 were tested and found to have excellent glucokinase activator in vivo activity when administered orally in advance with the assay described in Example B:

What is claimed is:

1. An amide compound of the formula:

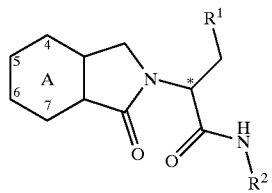

wherein
A is unsubstituted phenyl or phenyl which may be mono- or di-substituted with halo or mono-substituted with lower alkyl sulfonyl, lower alkyl thio or nitro;
$R^1$ is cycloalkyl having from 3 to 9 carbon atoms or lower alkyl having from 2 to 4 carbon atoms;
$R^2$ is an unsubstituted or mono-substituted five- or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom, which ring is monocyclic ring or fused with phenyl at two of its ring carbons, said mono-substituted heteroaromatic ring being monosubstituted at a position on a ring carbon atom other than adjacent to said connecting carbon atom with a substituent selected from the group consisting of halo, lower alkyl, nitro, cyano, perfluoro-lower alkyl; hydroxy, —$(CH_2)_n$—$OR^3$, —$(CH_2)_n$—$C(O)$—$OR^3$, —$(CH_2)_n$—$C(O)$—NH—$R^3$, —$C(O)C(O)$—$OR^3$, or —$(CH_2)_n$—$NHR^3$;
$R^3$ is hydrogen or lower alkyl; and
n is 0, 1, 2, 3 or 4;
or its pharmaceutically acceptable salt or N-oxide thereof.

2. The compound of claim 1 wherein said compound is said amide or its pharmaceutically acceptable salt thereof.

3. The compound of claim 2, wherein the amide is in the S configuration at the asymmetric carbon shown.

4. The compound of claim 2, wherein $R^2$ is substituted or unsubstituted pyridine.

5. The compound of claim 2, wherein $R^1$ is cycloalkyl having from 5 to 8 carbon atoms, and $R^2$ is an unsubstituted or mono-substituted five- or six-membered heteroaromatic ring connected by a ring carbon atom to the amine group shown, which five- or six-membered heteroaromatic ring contains from 1 to 2 heteroatoms selected from sulfur, oxygen or nitrogen, with one heteroatom being nitrogen which is adjacent to the connecting ring carbon atom, which ring is a monocyclic ring or a monocyclic ring fused with phenyl at two of its ring carbons, said mono-substituted heteroaromatic ring being monosubstituted at a position on a ring carbon atom other than adjacent to said connecting carbon atom with a substituent selected from the group consisting of halo or lower alkyl.

6. The compound of claim 2, wherein $R^1$ is cyclohexyl.

7. The compound of claim 6, wherein $R^2$ is a monocyclic ring.

8. The compound of claim 7, wherein $R^2$ is substituted or unsubstituted pyridine.

9. The compound of claim 8, wherein A is unsubstituted or halo substituted phenyl.

10. The compound of claim 9, wherein $R^2$ is unsubstituted pyridine.

11. The compound of claim 10, wherein said amide is (S)-3-cyclohexyl-2-(1-oxo-1,3-dihydro-isoindol-2-yl)-N-pyridin-2-yl-propionamide.

12. The compound of claim 9, wherein said amide is S)-3-cyclohexyl-2-(4-fluoro-1-oxo-1,3-dihydro-isoindol-2-yl)-N-pyridin-2-yl-propionamide and (S)-3-cyclohexyl-2-(7-fluoro-1-oxo-1,3-dihydro-isoindol-2-yl)-N-pyridin-2-yl-propionamide.

13. The compound of claim 9, wherein said amide is (S)-3-cyclohexyl-2-(4-chloro-1-oxo-1,3-dihydro-isoindol-2-yl)-N-pyridin-2-yl-propionamide and (S)-3-cyclohexyl-2-(7-chloro-1-oxo-1,3dihydro-isoindol-2-yl)-N-pyridin-2-yl-propionamide.

14. The compound of claim 9 wherein $R^2$ is monosubstituted pyridine.

15. The compound of claim 14, wherein said monosubstitution on said pyridine ring is halo.

16. The compound of claim 15, wherein said amide is (R)-N-(5-bromo-pyridin-2-yl)-3-cyclohexyl-2-(1-oxo-1,3-dihydro-isoindol-2-yl)-propionamide.

17. The compound of claim 15, wherein said amide is (S)-3-cyclohexyl-2-(1-oxo-1,3-dihydro-isoindol-2-yl)-N-5-chloro-pyridin-2-yl-propionamide.

18. The compound of claim 14, wherein said substituent on said pyridine is lower alkyl.

19. The compound of claim 18, wherein said amide is (S)-3-cyclohexyl-2-(1-oxo-1,3-dihydro-isoindol-2-yl)-N-4-methyl-pyridin-2-yl-propionamide.

20. The compound of claim 18, wherein said amide is (S)-3-cyclohexyl-2-(1-oxo-1,3dihydro-isoindol-2-yl)-N-5-methyl-pyridin-2-yl-propionamide.

21. The compound of claim 8, wherein $R^2$ is unsubstituted pyrimidine.

22. The compound of claim 21, wherein A is unsubstituted phenyl or is phenyl substituted with lower alkyl sulfonyl.

23. The compound of claim 22, wherein said amide is 3-cyclohexyl-2-(1-oxo-1,3-dihydro-isoindol-2-yl)-N-pyrimidin-4-yl-propionamide.

24. The compound of claim 22, wherein said amide is (S)-3-cyclohexyl-2-(4-methylsulfonyl-1-oxo-1,3-dihydro-isoindol-2-yl)-N-pyrimidin-4-yl-propionamide.

25. The compound of claim 22, wherein said amide is (S)-3-cyclohexyl-2-(7-methylsulfonyl-1-oxo-1,3-dihydro-isoindol-2-yl)-N-pyrimidin-4-yl-propionamide.

26. The compound of claim 8, wherein $R^2$ is a monosubstituted pyrimidine.

27. The compound of claim 26, wherein said substituent is lower alkyl.

28. The compound of claim 27, wherein A is unsubstituted phenyl.

29. The compound of claim 28, wherein said amide is (S)-N-3-cyclohexyl-N-(2-methyl-pyrimidin-4-yl)-2-(1-oxo-1,3-dihydro-isoindol-2-yl)-propionamide.

30. The compound of claim 7, wherein $R^2$ is unsubstituted thiazole.

31. The compound of claim 30, wherein A is unsubstituted phenyl.

32. The compound of claim 31, wherein said amide is (S)-3-cyclohexyl-2-(1-oxo-1,3-dihydro-isoindol-2-yl)-N-thiazol-2-yl-propionamide.

33. The compound of claim 31, wherein said amide is (R)-3-cyclohexyl-2-(1-oxo-1,3-dihydro-isoindol-2-yl)-N-thiazol-2-yl-propionamide.

34. The compound of claim 30, wherein A is chloro phenyl.

35. The compound of claim 34, wherein said amide is (S)-3-cyclohexyl-2-(5,6-dichloro-1-oxo-1,3-dihydro-isoindol-2-yl)-N-thiazol-2-yl-propionamide.

36. The compound of claim 30, wherein A is phenyl substituted with halo or lower alkyl sulfonyl.

37. The compound of claim 36, wherein said amide is (S)-3-cyclohexyl-2-(4-chloro-1-oxo-1,3-dihydro-isoindol-2-yl)-N-thiazol-2-yl-propionamide.

38. The compound of claim 36, wherein said amide is (S)-3-cyclohexyl-2-(4-fluoro-1-oxo-1,3-dihydro-isoindol-2-yl)-N-thiazol-2-yl-propionamide.

39. The compound of claim 36, wherein said amide is (S)-3-cyclohexyl-2-(7-fluoro-1-oxo-1,3dihydro-isoindol-2-yl)-N-thiazol-2-yl-propionamide.

40. The compound of claim 36, wherein said amide is (S)-3-cyclohexyl-2-(4-methylsulfonyl-1-oxo-1,3dihydro-isoindol-2-yl)-N-thiazol-2-yl-propionamide.

41. The compound of claim 36, wherein said amide is (S)-3-cyclohexyl-2-(7-methylsulfonyl-1-oxo-1,3-dihydro-isoindol-2-yl)-N-thiazol-2-yl-propionamide.

42. The compound of claim 30, wherein A is nitro phenyl.

43. The compound of claim 42, wherein said amide is (S)-3-cyclohexyl-2-(5-nitro-1-oxo-1,3-dihydro-isoindol-2-yl)-N-thiazol-2-yl -propionamide.

44. The compound of claim 42, wherein said amide is (S)-3-cyclohexyl-2-(6-nitro-1-oxo-1,3-dihydro-isoindol-2-yl)-N-thiazol-2-yl-propionamide.

45. The compound of claim 7, wherein $R^2$ is monosubstituted thiazole.

46. The compound of claim 45, wherein said monosubstituted thiazole is halo thiazole.

47. The compound of claim 46, wherein A is unsubstituted phenyl.

48. The compound of claim 47, wherein said amide is (S)-N-(5-chloro-thiazol-2-yl)-3-cyclohexyl-2-(1-oxo-1,3-dihydro-isoindol-2-yl) propionamide.

49. The compound of claim 47, wherein said amide is (S)-N-(5-bromo-thiazol-2-yl)-3-cyclohexyl-2-(1-oxo-1,3-dihydro-isoindol-2-yl)-propionamide.

50. The compound of claim 46, wherein A is phenyl substituted with halo.

51. The compound of claim 50, wherein said amide is (S)-N-(5-chloro-thiazol-2-yl)-3-cyclohexyl-2-(5,6-dichloro-1-oxo-1,3-dihydro-isoindol-2-yl)-propionamide.

52. The compound of claim 50, wherein said amide is (S)-N-(5-bromo-thiazol-2-yl)-3-cyclohexyl-2-(5,6-dichloro-1-oxo-1,3-dihydro-isoindol-2-yl)-propionamide.

53. The compound of claim 50, wherein said amide is (S)-N-(5-chloro-thiazol-2-yl)-3-cyclohexyl-2-(4-chloro-1-oxo-1,3-dihydro-isoindol-2-yl)-propionamide and (S)-N-(5-chloro-thiazol-2-yl)-3-cyclohexyl-2-(7-chloro-1-oxo-1,3-dihydro-isoindol-2-yl)-propionamide.

54. The compound of claim 46, wherein A is phenyl substituted with nitro.

55. The compound of claim 54, wherein said amide is (S)-N-(5-chloro-thiazol-2-yl)-3-cyclohexyl-2-(5-nitro-1-oxo-1,3-dihydro-isoindol-2-yl)-propionamide.

56. The compound of claim 54, wherein said amide is (S)-N-(5-chloro-thiazol-2-yl)-3-cyclohexyl-2-(6-nitro-1-oxo-1,3-dihydro-isoindol-2-yl)-propionamide.

57. The compound of claim 46, wherein A is phenyl substituted with fluoro.

58. The compound of claim 57, wherein said amide is (S)-N-(5-chloro-thiazol-2-yl)-3-cyclohexyl-2-(4-fluoro-1-oxo-1,3-dihydro-isoindol-2-yl)-propionamide.

59. The compound of claim 57, wherein said amide is (S)-N-(5-chloro-thiazol-2-yl)-3-cyclohexyl-2-(7-fluoro-1-oxo-1,3-dihydro-isoindol-2-yl)-propionamide.

60. The compound of claim 7, wherein $R^2$ is an unsubstituted pyrazine.

61. The compound of claim 60, wherein A is phenyl substituted with lower alkyl sulfonyl or fluoro.

62. The compound of claim 61, wherein said amide is (S)-3-cyclohexyl-2-(4-fluoro-1-oxo-1,3dihydro-isoindol-2-yl)-N-pyrazin-2-yl-propionamide.

63. The compound of claim 61, wherein said amide is (S)-3-cyclohexyl-2-(7-fluoro-1-oxo-1,3-dihydro-isoindol-2-yl)-N-pyrazin-2-yl-propionamide.

64. The compound of claim 64, wherein said amide is (S)-3-cyclohexyl-2-(4-methylsulfonyl-1-oxo-1,3-dihydro-isoindol-2-yl)-N-pyrazin-2-yl-propionamide.

65. The compound of claim 61, wherein said amide is (S)-3-cyclohexyl-2-(7-methylsulfonyl-1-oxo-1,3-dihydro-isoindol-2-yl)-N-pyrazin-2-yl-propionamide.

66. The compound of claim 60, wherein A is unsubstituted or halo substituted phenyl.

67. The compound of claim 66, wherein said amide is (S)-3-cyclohexyl-2-(1-oxo-1,3dihydro-isoindol-2-yl)-N-pyrazin-2-yl-propionamide.

68. The compound of claim 66, wherein said amide is (S)-3-cyclohexyl-2-(4-chloro-1-oxo-1,3-dihydro-isoindol-2-yl)-N-pyrazin-2-yl-propionamide.

69. The compound of claim 7, wherein A is unsubstituted phenyl.

70. The compound of claim 69, wherein $R^2$ is unsubstituted imidazole.

71. The compound of claim 60, wherein said amide is (S)-3-cyclohexyl-N-(1H-imidazol-2-yl)-2-(1-oxo-1,3-dihydro-isoindol-2-yl) propionamide.

72. The compound of claim 2, wherein A is unsubstituted phenyl.

73. The compound of claim 72, wherein $R^2$ is a monocyclic ring.

74. The compound of claim 73, wherein $R^2$ is substituted or unsubstituted thiazole.

75. The compound of claim 74, wherein $R^1$ is cyclopentyl.

76. The compound of claim 75, wherein said amide is 3-cyclopentyl-2-(1-oxo-1,3-dihydro-isoindol-2-yl)-N-thiazol-2-yl-propionamide.

77. The compound of claim 75, wherein said amide is N-(5-chloro-thiazol-2-yl)-3-cyclopentyl-2-(1-oxo-1,3-dihydro-isoindol-2-yl)-propionamide.

78. The compound of claim 78, wherein $R^1$ is cycloheptyl.

79. The compound of claim 78, wherein said amide is 3-cycloheptyl-2-(1-oxo-1,3-dihydro-isoindol-2-yl)-N-thiazol-2-yl-propionamide.

80. The compound of claim 78, wherein said amide is N-(5-chloro-thiazol-2-yl)-3-cycloheptyl-2-(1-oxo-1,3-dihydro-isoindol-2-yl)-propionamide.

81. The compound of claim 74, wherein $R^1$ is cyclooctyl.

82. The compound of claim 81, wherein said amide is 3-cyclooctyl-2-(1-oxo-1,3-dihydro-isoindol-2-yl)-N-thiazol-2-yl-propionamide.

83. The compound of claim 2, wherein $R^2$ is fused with phenyl at two of its ring carbons.

84. The compound of claim 83, wherein $R^1$ is cyclohexyl.

85. The compound of claim 84, wherein A is unsubstituted phenyl.

86. The compound of claim 85, wherein $R^2$ is unsubstituted benzthiazole.

87. The compound of claim 86, wherein said amide is (S)-N-benzothiazol-2-yl-3-cyclohexyl-2-(1-oxo-1,3-dihydro-isoindol-2-yl)-propionamide.

88. The compound of claim 87, wherein $R^2$ is unsubstituted benzimidazole.

89. The compound of claim 88, wherein said amide is (S)-N-(1-H-benzoimidazol-2-yl)-3-cyclohexyl-2-(1-oxo-1,3-dihydro-isoindol-2-yl)-propionamide.

90. The compound of claim 85, wherein $R^2$ is unsubstituted benzoxazole.

91. The compound of claim 90, wherein said amide is (S)-N-benzooxazol-2-yl-3-cyclohexyl-2-(1-oxo-1,3-dihydro-isoindol-2-yl)-propionamide.

92. The compound of claim 91, wherein $R^2$ is unsubstituted quinoline.

93. The compound of claim 92, wherein said amide is (S)-3-cyclohexyl-2-(1-oxo-1,3-dihydro-isoindol-2-yl)-N-quinolin-2-yl-propionamide.

94. The compound of claim 1, wherein said amide is N-oxide of the ring nitrogen atom in the heterocyclic nitrogen containing ring formed by $R^2$.

95. A compound of claim 95 wherein $R^2$ is pyridine.

96. The compound of claim 96, wherein said amide is S-3-cyclohexyl-2-(1-oxo-1,3-dihydro-isoindol-2-yl)-N-(1-oxy-pyridin-2-yl)-propionamide.

97. The compound of claim 37, wherein said amide is (S)-3-cyclohexyl-2-(7-chloro-1-oxo-1,3dihydro-isoindol-2-yl)-N-thiazol-2-yl-propionamide.

* * * * *